(12) United States Patent
Takahashi et al.

(10) Patent No.: US 10,919,872 B2
(45) Date of Patent: Feb. 16, 2021

(54) METHOD FOR PRODUCING 2-ALKYLCARBONYLNAPHTHO[2,3-B]FURAN-4,9-DIONE-RELATED SUBSTANCE, AND SAID RELATED SUBSTANCE

(71) Applicant: Sumitomo Dainippon Pharma Co., Ltd., Osaka (JP)

(72) Inventors: Kazuhiko Takahashi, Osaka (JP); Shoji Watanabe, Osaka (JP); Katsuya Uchiyama, Osaka (JP); Kento Senami, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 16/851,389

(22) Filed: Apr. 17, 2020

(65) Prior Publication Data

US 2020/0239424 A1 Jul. 30, 2020

Related U.S. Application Data

(62) Division of application No. 16/086,759, filed as application No. PCT/JP2017/012046 on Mar. 24, 2017.

(30) Foreign Application Priority Data

Mar. 25, 2016 (JP) .............................. JP2016-061242

(51) Int. Cl.
*C07D 307/92* (2006.01)

(52) U.S. Cl.
CPC ............ *C07D 307/92* (2013.01); *Y02P 20/55* (2015.11)

(58) Field of Classification Search
CPC .............................. C07D 307/92; Y02P 20/55
USPC .......................................................... 549/458
See application file for complete search history.

(56) References Cited

U.S. PATENT DOCUMENTS

| | | | | |
|---|---|---|---|---|
| 2011/0112180 A1* | 5/2011 | Jiang | .................... | A61P 7/00 514/443 |
| 2012/0077986 A1* | 3/2012 | Iida | .................... | C07D 209/60 548/427 |
| 2015/0191478 A1 | 7/2015 | Seo et al. | | |

FOREIGN PATENT DOCUMENTS

| | | |
|---|---|---|
| JP | 2012-92083 | 5/2012 |
| JP | 5208239 | 6/2013 |
| WO | 2009/036099 | 3/2009 |
| WO | 2012/119265 | 9/2012 |
| WO | 2016/157052 | 10/2016 |

OTHER PUBLICATIONS

International Search Report dated May 23, 2017 in International (PCT) Application No. PCT/JP2017/012046.
Zubia et al., "An efficient synthesis of furanocoumarins", Tetrahedron, vol. 48, No. 20, 1992, pp. 4239-4246.
Nordvall. et al., "3-(2-Benzofuranyl)quinuclidin-2-ene Derivatives: Novel Muscarinic Antagonists", Journal of Medicinal Chemistry, vol. 39, No. 17, 1996, pp. 3269-3277.
Inagaki, et al., "Synthesis and cytotoxicity on human leukemia cells of furonaphthoquinones isolated from *Tabebuia* plants", Chemical & Pharmaceutical Bulletin, vol. 61, No. 6, 2013, pp. 670-673.
Rao et al., "Plant anticancer agents. XII Isolation and structure elucidation of new cytotoxic quinones from *Tabebuia cassinoides*", Journal of Natural Products, vol. 45, No. 5, 1982, pp. 600-604.
Shvartsberg et al., "Acetylenic derivatives of quinones", Russian Chemical Review, vol. 73, No. 2, 2004, pp. 161-184.
Macharla et al., "Oxidative bromination of ketones using ammonium bromide and oxone", Tetrahedron Letters, vol. 53, 2012, pp. 191-195.
Reddy et al., "Oxidative iodination of carbonyl compounds using ammonium iodide and oxone", Tetrahedron Letters, vol. 52, 2011, pp. 6554-6559.
Hatzigrigoriou et al., "Derivatives of 1,4-Naphthoquinone via 3-(Phenyliodonio)-1,2,4-trioxo-1,2,3,4-Tetrahydronaphthalenide", Liebigs Ann. Chem, vol. 2, 1989, pp. 167-170.

* cited by examiner

*Primary Examiner* — Taylor V Oh
(74) *Attorney, Agent, or Firm* — Wenderoth, Lind & Ponack, L.L.P.

(57) ABSTRACT

Provided is a method for producing a 2-alkylcarbonylnaphtho[2,3-b]furan-4,9-dione-related substance, which is suitable for the production on an industrial scale. The present invention provides: a method for producing an intermediate for the production of a 2-alkylcarbonyl[2,3-b]furan-4,9-dione, which comprises reacting a 1-butyne derivative in which a ketone or an alcohol is protected with a 2-hydroxy-1,4-naphthoquinone derivative having a leaving group at position-3 in a solvent in the presence of a metal or a metal compound and a base; and a substance relating to the intermediate.

19 Claims, No Drawings

METHOD FOR PRODUCING 2-ALKYLCARBONYLNAPHTHO[2,3-B]FURAN-4,9-DIONE-RELATED SUBSTANCE, AND SAID RELATED SUBSTANCE

TECHNICAL FIELD

The present invention relates to a method of producing 2-alkylcarbonylnaphtho[2,3-b]furan-4,9-dione related substances that are useful as a pharmaceutical product and said related substances.

BACKGROUND ART

As a method of producing 2-acetylnaphtho[2,3-b]furan-4,9-dione and a method of producing related substances, the methods described in for example Patent Literatures 1 and 2 and Non Patent Literature 1 are known. As a method of producing a naphtho[2,3-b]furan-4,9-dione backbone with a substituent at position 2, the methods described in Patent Literature 3 and Non Patent Literature 2 are known.

In Patent Literature 1, Li et al. obtains 3-bromo-3-buten-2-one by dibrominating 3-buten-2-one with bromine, followed by dehydrobromination using DBU (1,8-diazabicyclo[5.4.0]-7-undecene). Subsequently, 3-bromo-3-buten-2-one and 2-hydroxy-1,4-naphthoquinone are coupled to obtain 2-acetyl-2,3-dihydronaphtho[2,3-b]furan-4,9-dione. A method of obtaining 2-acetylnaphtho[2,3-b]furan-4,9-dione by oxidizing said intermediate has been reported.

In Patent Literature 2, Jiang et al. obtains 2-acetyl-2,3-dihydronaphtho[2,3-b]furan-4,9-dione by brominating 3-buten-2-one with bromine, and dehydrobrominating with DBU to obtain 3-bromo-3-buten-2-one, and then adding 2-hydroxy-1,4-naphthoquinone into the reaction system and allowing the mixture to condensate under an ambient atmosphere. Subsequently, 2-acetyl-2,3-dihydronaphtho[2,3-b]furan-4,9-dione is stirred under ambient atmosphere with DBU to obtain 2-acetylnaphtho[2,3-b]furan-4,9-dione.

The method in Patent Literature 2 has a low synthesis yield of 2-acetyl-2,3-dihydronaphtho[2,3-b]furan-4,9-dione and low purity of said intermediate. The yield of 2-acetylnaphtho[2,3-b]furan-4,9-dione is also not high with the method of Patent Literature 2.

In Non Patent Literature 1, Inagaki et al. obtains 2-(1-hydroxyethyl)naphtho[2,3-b]furan-4,9-dione, which is an intermediate with a naphtho[2,3-b]furan-4,9-dione backbone, by reacting 3-phenyliodonio-1,2,4-trioxo-1,2,3,4-tetrahydronaphthalenide obtained from 2-hydroxy-1,4-naphthoquinone and iodobenzene diacetate with 10 equivalents of 3-butyne-2-ol under Sonogashira coupling conditions. A hydroxyethyl group of said 2-(1-hydroxyethyl)naphtho[2,3-b]furan-4,9-dione is oxidized to obtain 2-aceylnaphtho[2,3-b]furan-4,9,dione.

In Patent Literature 3, as a method of constructing a naphtho[2,3-b]furan-4,9-dione backbone with a substituent at position 2, Iida et al. reacts 3-bromo-2-dimethylamino-juglone (also known as: 3-bromo-2-(dimethylamino)-5-hydroxynaphthalene-4,9-dione) and 10 equivalents of (S)-(–)-3-butyne-2-ol using Sonogashira coupling conditions to obtain 2-dimethylamino-3-(3-hydroxybut-1-yn-1-yl)juglone (also known as: 2-dimethylamino-5-hydroxy-3-(3-hydroxybut-1-yn-1-yl)naphthalene-1,4-dione), which is then heated in hydrous methanol to obtain (-)-2-(1-hydroxyethyl)-5-hydroxynaphtho[2,3-b]furan-4,9-dione. In Patent Literature 3, 2-(1-hydroxyethyl)-5-hydroxynaphtho[2,3-b]furan-4,9-dione is also obtained by reacting 2,5-dihydroxy-3-iodonaphthalene-1,4-dione and 10 equivalents of 3-butyne-2-ol under Sonogashira coupling conditions.

The method described in Non Patent Literature 1 or Patent Literature 3 uses 10 equivalents of acetylene compounds to a substrate when constructing a naphtho[2,3-b]furan-4,9-dione backbone with a substitution at position 2. Furthermore, the product has poor stability and the reaction yield is low. In addition, there are palladium residues in a pharmaceutical product due to the use of a palladium catalyst.

Non Patent Literature 2 discloses an example of constructing a naphtho[2,3-b]furan-4,9-dione backbone by reacting copper acetylide and 2-hydroxy-1,4-naphthoquinone, with brominated or iodinated position 3, as a reaction example for constructing a naphtho[2,3-b]furan-4,9-dione backbone with a substitution at position 2. However, said reaction needs to first isolate copper acetylide for use. Furthermore, Non Patent Literature 2 does not disclose a specific intermediate from which 2-alkylcarbonylnaphtho[2,3-b]furan-4,9-dione can be derived, and the reaction yield is also low.

CITATION LIST

Patent Literature

[PTL 1] International Publication No. WO 2009/036099
[PTL 2] International Publication No. WO 2012/119265
[PTL 3] Japanese Patent No. 5208239

Non Patent Literature

[NPL 1] R. Inagaki, et al., Chem. Pharm. Bull. 61, 670 (2013)
[NPL 2] S. Shvartsberg, et al., Russian Chemical Review 73(2), p. 161-184 (2004)

SUMMARY OF INVENTION

Solution to Problem

The present invention provides a method of producing 2-alkylcarbonylnaphtho[2,3-b]furan-4,9-dione related substances that are suitable for industrial production, and said related substances. In other words, the present invention provides a method of constructing a 2-substituted naphtho[2,3-b]furan-4,9-dione backbone safely, readily, at a high yield and with high purity.

More specifically, the inventors have found as a result of diligent research that a "naphtho[2,3-b]furan-4,9-dione backbone with a substitution at position 2 (I)", which is an intermediate that is useful in producing 2-alkylcarbonylnaphtho[2,3-b]furan-4,9-dione, can surprisingly be constructed at a high yield by reacting "2-hydroxy-1,4-naphthoquinone with a leaving group at position 3 (1)" with an "acetylene compound (2)" in a solvent in the presence of a metal or a metal compound and a base. It was also found that 2-alkylcarbonylnaphtho[2,3-b]furan-4,9-dione can be produced readily and at a high yield from said intermediate.

[Chemical formula 1]

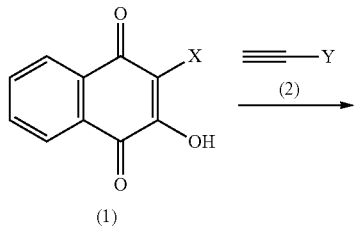

-continued

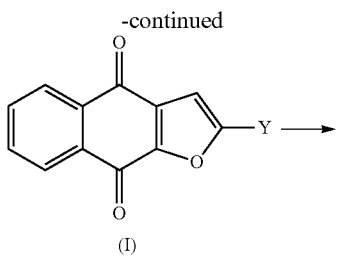

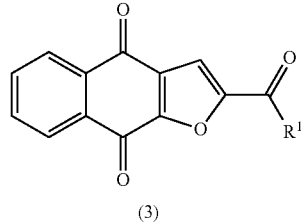

2-alkylcarbonylnaphtho[2,3-b]furan-4,9-dione

In other words, the present invention is the following.

(Item 1)

A production method of a compound of formula (I):

[Chemical formula 2]

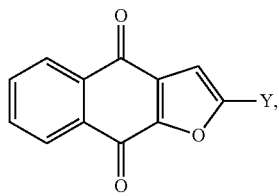

or a tautomer thereof, or an optionally pharmaceutically acceptable salt thereof or solvate thereof, wherein Y is a group represented by the following formula (Ya), (Yb), or (Yc):

[Chemical formula 3]

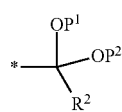
(Ya)

[Chemical formula 4]

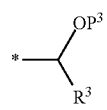
(Yb)

[Chemical formula 5]

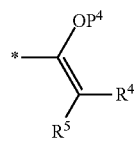
(Yc)

wherein
* denotes a bonding position;
$P^1$ and $P^2$ are identical or different, and each independently a protecting group for a carbonyl group, or are taken together to form a protecting group, where $P^1$ and $P^2$ are not both hydrogen atoms;
$P^3$ is a hydrogen atom or a protecting group for a hydroxyl group;
$P^4$ is a protecting group for a hydroxyl group;
$R^2$ is an optionally substituted $C_{1-10}$alkyl group;
$R^3$ is an optionally substituted $C_{1-10}$alkyl group; and
$R^4$ and $R^5$ are identical or different, and each independently a hydrogen atom or an optionally substituted $C_{1-10}$alkyl group, the production method comprising the following step (a):

(a)

a step of reacting a compound of formula (1):

[Chemical formula 6]

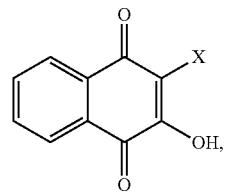

or a tautomer thereof, or an optionally pharmaceutically acceptable salt thereof or solvate thereof, wherein X is a leaving group, in a solvent in the presence of a metal or a metal compound and a base with a compound of formula (2):

[Chemical formula 7]

$$\equiv\!\!-\!\!Y,\qquad(2)$$

or a tautomer thereof, or an optionally pharmaceutically acceptable salt thereof or solvate thereof, wherein Y is defined the same as the above, to produce a compound of formula (I):

[Chemical formula 8]

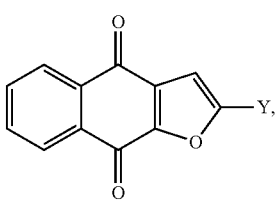

or a tautomer thereof, or an optionally pharmaceutically acceptable salt thereof or solvate thereof, wherein Y is defined the same as the above.

[Item 2]

The production method according to item 1, characterized in that the base used in the step (a) is an organic base.

[Item 3]

The production method according to item 1 or 2, wherein the base used in the step (a) comprises N-methylpiperidine, 1,4-diazabicyclo[2.2.2]octane, N,N,N',N'-tetramethylethane-1,2-diamine, pyrimidine, 2-picoline, 3-picoline, 4-picoline, 2-pyridinemethanol, 2,4-lutidine, 2,5-lutidine, 2,6-lutidine, 2,4,6-collidine, or pyridine.

[Item 4]

The production method according to any one of items 1 to 3, characterized in that the base used in the step (a) is pyridine and the base is used as the solvent.

[Item 5]

The production method according to any one of items 1 to 4, wherein the metal or metal compound used in the step (a) is metal copper or a copper compound.

[Item 6]

The production method according to any one of items 1 to 5, wherein the metal or metal compound used in the step (a) is metal copper(0) or copper(I) oxide.

[Item 7]

The production method according to any one of items 1 to 6, characterized in that neither metal palladium nor palladium compound is used in the step (a).

[Item 8]

The production method according to any one of items 1 to 7, wherein X is a halogen atom, an optionally substituted iodonio group, an optionally substituted sulfonyloxy group, or an optionally substituted phosphoryloxy group.

[Item 9]

The production method according to any one of items 1 to 8, wherein X is a fluorine atom, a chlorine atom, a bromine atom, an iodine atom, a phenyliodonio group, a methanesulfonyloxy group, an ethanesulfonyloxy group, a trifluoromethanesulfonyloxy group, a chlorosulfonyloxy group, a benzenesulfonyloxy group, or a p-toluenesulfonyloxy group.

[Item 10]

The production method according to any one of items 1 to 9, wherein X is a bromine atom, an iodine atom, or a phenyliodonio group.

[Item 11]

The production method according to any one of items 1 to 10, wherein X is a bromine atom.

[Item 12]

The production method according to any one of items 1 to 11, wherein $P^1$ and $P^2$ are identical or different, and each independently (1) a hydrogen atom, (2) an optionally substituted $C_{1-10}$alkyl group, (3) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group), (4) an optionally substituted $C_{6-10}$aryl group, (5) an optionally substituted $C_{1-10}$alkylcarbonyl group, (6) an optionally substituted $C_{6-10}$arylcarbonyl group, or (7) an optionally substituted $C_{3-10}$cycloalkyl group; and wherein when $P^1$ and $P^2$ are identical or different, and each independently an optionally substituted $C_{1-10}$alkyl group, an optionally substituted $C_{6-10}$aryl group, an optionally substituted $C_{1-10}$alkylcarbonyl group, or an optionally substituted $C_{3-10}$cycloalkyl group, they may be taken together to form an optionally substituted cyclic ketal, and $P^1$ and $P^2$ are not both hydrogen atoms.

[Item 13]

The production method according to any one of items 1 to 12, wherein $P^1$ and $P^2$ are identical or different, and each independently (1) a hydrogen atom, (2) a $C_{1-6}$alkyl group optionally substituted with one to three groups independently selected from the group consisting of a halogen atom and a $C_{1-6}$alkoxy group, (3) a silyl group optionally substituted with one to three $C_{1-6}$alkyl groups, (4) a phenyl group, (5) a benzyl group, or (6) a $C_{1-6}$alkylcarbonyl group; or $P^1$ and $P^2$ may be taken together to form a cyclic ketal selected from the group consisting of (7) 1,3-dioxolane optionally substituted with one to four groups independently selected from the group consisting of a $C_{1-6}$alkyl group, a $C_{1-6}$alkoxy group, a hydroxyl group, and a phenyl group, (8) 1,3-dioxolane-4-one, (9) 1,3-dioxolane-4,5-dione,

(10) 1,3-dioxane optionally substituted with one to four groups independently selected from the group consisting of a $C_{1-6}$alkyl group, a $C_{1-6}$alkoxy group, a hydroxyl group, and a phenyl group,

(11) 1,3-dioxane-4-one,

(12) 1,3-dioxane-4,6-dione, and

(13) benzo[d][1,3]dioxole, and $P^1$ and $P^2$ are not both hydrogen atoms.

[Item 14]

The production method according to any one of items 1 to 13, wherein $P^1$ and $P^2$ are identical or different, and each independently a $C_{1-6}$alkyl group or a $C_{1-6}$alkylcarbonyl group, or $P^1$ and $P^2$ are taken together to form a cyclic ketal selected from the group consisting of 1,3-dioxolane optionally substituted with one to four $C_{1-6}$alkyl groups, and 1,3-dioxane optionally substituted with one to four $C_{1-6}$alkyl groups.

[Item 15]

The production method according to any one of items 1 to 14, wherein $P^1$ and $P^2$ are identical or different, and each independently a methyl group, an ethyl group, a propyl group, an isopropyl group, a butyl group, a tert-butyl group, a pentyl group, or an acetyl group, or $P^1$ and $P^2$ are taken together to form a cyclic ketal selected from the group consisting of 1,3-dioxolane, 4-methyl-1,3-dioxolane, 4,5-dimethyl-1,3-dioxolane, 4,4,5,5-tetramethyl-1,3-dioxolane, 1,3-dioxane, 4-methyl-1,3-dioxane, 5-methyl-1,3-dioxane, and 5,5-dimethyl-1,3-dioxane.

[Item 16]

The production method according to any one of items 1 to 15, wherein $P^1$ and $P^2$ are taken together to form 1,3-dioxolane or 1,3-dioxane.

[Item 17]

The production method according to any one of items 1 to 16, wherein $R^2$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 18]

The production method according to any one of items 1 to 17, wherein $R^2$ is a $C_{1-6}$alkyl group.

[Item 19]

The production method according to any one of items 1 to 18, wherein $R^2$ is a methyl group.

[Item 20]

The production method according to any one of items 1 to 19, wherein $P^3$ is
(1) an optionally substituted $C_{1-10}$alkyl group,
(2) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group),
(3) an optionally substituted 3- to 12-membered monocyclic or polycyclic heterocyclic group (wherein in the heterocyclic group, a carbon atom adjacent to a heteroatom in the ring is bound to the oxygen atom to which $P^3$ in the formula (Yb) is attached),
(4) an optionally substituted $C_{2-10}$alkenyl group,
(5) an optionally substituted $C_{6-10}$aryl group,
(6) an optionally substituted $C_{1-10}$alkylcarbonyl group,
(7) an optionally substituted $C_{6-10}$arylcarbonyl group,
(8) an optionally substituted $C_{1-10}$alkyloxycarbonyl group,
(9) an optionally substituted $C_{6-10}$aryloxycarbonyl group,
(10) an optionally substituted $C_{2-10}$alkenyloxycarbonyl group,
(11) an optionally substituted aminocarbonyl group,
(12) an optionally substituted $C_{1-10}$alkylsulfonyl group,
(13) an optionally substituted $C_{6-10}$arylsulfonyl group,
(14) a formyl group, or
(15) a hydrogen atom.

[Item 21]

The production method according to any one of items 1 to 20, wherein $P^3$ is
(1) a $C_{1-6}$alkyl group (the alkyl group is optionally substituted with one to three groups independently selected from the group consisting of
   (a) a halogen atom,
   (b) a $C_{1-6}$alkoxy group,
   (c) a silyloxy group substituted with three groups independently selected from the group consisting of a $C_{1-6}$alkyl group and a phenyl group,
   (d) a silyl group substituted with three groups independently selected from the group consisting of a $C_{1-6}$alkyl group and a phenyl group, and
   (e) a phenyl group optionally substituted with one to three groups independently selected from the group consisting of a halogen atom, a methoxy group, and a nitro group);
(2) a silyl group substituted with three substituents independently selected from the group consisting of a $C_{1-6}$alkyl group and a phenyl group;
(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^3$ in the formula (Yb) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{1-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups);
(14) a formyl group; or
(15) a hydrogen atom.

[Item 22]

The production method according to any one of items 1 to 21, wherein $P^3$ is
(1) a $C_{1-6}$alkyl group (the alkyl group is optionally substituted with 1 to 3 groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached),
(6) a $C_{2-6}$alkenyl group,
(7) a $C_{1-6}$alkylcarbonyl group (the alkyl is optionally substituted with 1 to 3 fluorine atoms),
(8) a $C_{1-6}$alkyloxycarbonyl group,
(9) a benzyloxycarbonyl group,
(10) an allyloxycarbonyl group, or
(11) a hydrogen atom.

[Item 23]

The production method according to any one of items 1 to 22, wherein $P^3$ is
(1) a $C_{1-6}$alkyl group optionally substituted with one to three $C_{1-6}$alkoxy groups,
(2) a silyl group substituted with three substituents independently selected from the group consisting of a $C_{1-6}$ alkyl group and a phenyl group, or
(3) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached).

[Item 24]

The production method according to any one of items 1 to 23, wherein $P^3$ is a methoxymethyl group, a tert-butyl group, a 1-ethoxyethyl group, a 2-tetrahydropyranyl group, a 2-tetrahydrofuranyl group, a trimethylsilyl group, a triethylsilyl group, or a tert-butyldimethylsilyl group.

[Item 25]

The production method according to any one of items 1 to 24, wherein $P^3$ is a 2-tetrahydropyranyl group, a trimethylsilyl group, or a tert-butyldimethylsilyl group.

[Item 26]

The production method according to any one of items 1 to 25, wherein $R^3$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 27]

The production method according to any one of items 1 to 26, wherein $R^3$ is a $C_{1-6}$alkyl group.

[Item 28]

The production method according to any one of items 1 to 27, wherein $R^3$ is a methyl group.

[Item 29]

The production method according to any one of items 1 to 28, wherein $P^4$ is (1) an optionally substituted $C_{1-10}$alkyl group;
(2) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group);
(3) an optionally substituted 3- to 12-membered monocyclic or polycyclic heterocyclic group (wherein in the heterocyclic group, a carbon atom adjacent to a heteroatom in the ring is bound to the oxygen atom to which $P^4$ in the formula (Yc) is attached);
(4) an optionally substituted $C_{2-10}$alkenyl group;
(5) an optionally substituted $C_{6-10}$aryl group;
(6) an optionally substituted $C_{1-10}$alkylcarbonyl group;
(7) an optionally substituted $C_{6-10}$arylcarbonyl group;
(8) an optionally substituted $C_{1-10}$alkyloxycarbonyl group;
(9) an optionally substituted $C_{6-10}$aryloxycarbonyl group;
(10) an optionally substituted $C_{2-10}$alkenyloxycarbonyl group;
(11) an optionally substituted aminocarbonyl group;
(12) an optionally substituted $C_{1-10}$alkylsulfonyl group;
(13) an optionally substituted $C_{6-10}$arylsulfonyl group; or
(14) a formyl group.

[Item 30]

The production method according to any one of items 1 to 29, wherein $P^4$ is (1) a $C_{1-6}$alkyl group (the alkyl group is optionally substituted with one to three groups independently selected from the group consisting of
  (a) a halogen atom,
  (b) a $C_{1-6}$alkoxy group
  (c) a silyloxy group substituted with three groups independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group);
(2) a silyl group substituted with three substituents independently selected from the group consisting of a $C_{1-6}$alkyl group and a phenyl group;
(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^4$ in the formula (Yc) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{1-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups); or
(14) a formyl group.

[Item 31]

The production method according to any one of items 1 to 30, wherein $P^4$ is (1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^4$ in the formula (Yc) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group, or
(10) an allyloxycarbonyl group.

[Item 32]

The production method according to any one of items 1 to 31, wherein $P^4$ is (1) a $C_{1-6}$alkyl group optionally substituted with one to three $C_{1-6}$alkoxy groups;
(2) a silyl group substituted with three substituents independently selected from the group consisting of a $C_{1-6}$alkyl group and a phenyl group; or
(3) a 5- or 6-membered monocyclic saturated heterocyclic group (wherein the saturated heterocyclic group has at least one or more oxygen atoms in the ring and a carbon atom adjacent to the oxygen atom(s) is bound to the oxygen atom to which $P^4$ in the formula (Yc) is attached).

[Item 33]

The production method according to any one of items 1 to 32, wherein $P^4$ is a methoxymethyl group, a tert-butyl group, a 1-ethoxyethyl group, a 2-tetrahydropyranyl group, a 2-tetrahydrofuranyl group, a trimethylsilyl group, a triethylsilyl group, or a tert-butyldimethylsilyl group.

[Item 34]

The production method according to any one of items 1 to 33, wherein $P^4$ is a 2-tetrahydropyranyl group, a trimethylsilyl group, or a tert-butyldimethylsilyl group.

[Item 35]

The production method according to any one of items 1 to 34, wherein $R^4$ and $R^5$ are identical or different, and each independently (1) a hydrogen atom, or (2) a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 36]

The production method according to any one of items 1 to 35, wherein $R^4$ and $R^5$ are identical or different, and each independently (1) a hydrogen atom, or (2) a $C_{1-6}$alkyl group.

[Item 37]

The production method according to any one of items 1 to 36, wherein $R^4$ and $R^5$ are hydrogen atoms.

[Item 38]

The production method according to any one of items 1 to 19, wherein Y is a group represented by the formula (Ya).

[Item 39]

The production method according to item 38, further comprising the following step (b) after the step (a):

(b)

a step of deprotecting $P^1$ and $P^2$, which are protecting groups for a carbonyl group of the compound represented by formula (I), or a tautomer thereof, or an optionally pharmaceutically acceptable salt thereof, obtained in the step (a), to produce a compound of formula (3):

[Chemical formula 9]

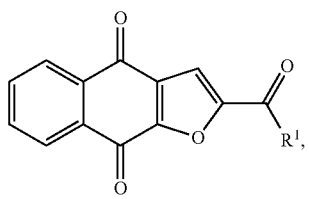

(3)

or a tautomer thereof, or an optionally pharmaceutically acceptable salt thereof or solvate thereof, wherein $R^1$ is defined the same as the above $R^2$.

[Item 39A]

The production method according to item 39, comprising a step of purifying a product of the step (a).

[Item 39B]

The production method according to item 39A, wherein a solvent used in step (b) is water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, or a mixture solvent thereof.

[Item 39C]

The production method according to item 39, wherein the step (b) is performed without purifying a product of the step (a).

[Item 39D]

The production method according to item 39C, wherein a solvent used in step (b) is a solvent that can be exchanged with a solvent used in step (a).

[Item 39E]

The production method according to item 39D, wherein the solvent used in step (a) is pyridine, and the solvent used in step (b) is water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, or a mixture solvent thereof.

[Item 40]

The production method according to any one of items 1 to 11 and 20 to 28, wherein Y is a group represented by the formula (Yb).

[Item 41]

The production method according to item 40, further comprising the following step (c) after the step (a):

(c)

a step of deprotecting $P^3$ when $P^3$ of the compound represented by formula (I), or a tautomer thereof, or an optionally pharmaceutically acceptable salt thereof or solvate thereof, obtained in the step (a), is not a hydrogen atom, to produce a compound of formula (4):

[Chemical formula 10]

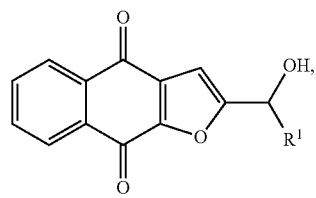

(4)

or a tautomer thereof, or an optionally pharmaceutically acceptable salt thereof or solvate thereof, wherein $R^1$ is defined the same as the above $R^3$.

[Item 42]

The production method according to item 40 or 41, further comprising the following step (d) after the step (a) or (c):

(d)

a step of oxidizing the compound represented by formula (I) or (4), or a tautomer thereof, or an optionally pharmaceutically acceptable salt thereof or solvate thereof, obtained in the step (a) or (c), using an oxidant to produce a compound of formula (3):

[Chemical formula 11]

(3)

or a tautomer thereof, or an optionally pharmaceutically acceptable salt thereof or solvate thereof, wherein $R^1$ is defined the same as the above $R^3$.

[Item 43]

The production method according to item 42, wherein the oxidant used in the step (d) is chromium oxide, chromic acid, pyridinium chlorochromate, pyridinium dichromate, sodium dichromate, manganese dioxide, sodium hypochlorite, sodium bromite, N-chlorosuccinimide, N-bromosuccinimide, dimethyl sulfoxide, 2,2,6,6-tetramethylpiperidine-1-oxyl, 2-azaadamantane-N-oxyl, or 1-methyl-2-azaadamantane-N-oxyl.

[Item 44]

The production method according to any one of items 1 to 11 and 29 to 37, wherein Y is a group represented by the formula (Yc).

[Item 45]

The production method according to item 44, further comprising the following step (e) after the step (a):
(e)
a step of deprotecting $P^4$, which is a protecting group for a hydroxyl group of the compound represented by formula (I), or a tautomer thereof, or an optionally pharmaceutically acceptable salt thereof or solvate thereof, obtained in the step (a), to produce a compound of formula (3):

[Chemical formula 12]

(3)

or a tautomer thereof, or an optionally pharmaceutically acceptable salt thereof or solvate thereof, wherein $R^1$ is defined the same as $CHR^4R^5$.

[Item 46]

A compound of formula (I):

[Chemical formula 13]

(I)

or a tautomer thereof, or an optionally pharmaceutically acceptable salt thereof, wherein Y is a group represented by the following formula (Ya), (Yb), or (Yc):

[Chemical formula 14]

(Ya)

[Chemical formula 15]

(Yb)

[Chemical formula 16]

(Yc)

wherein
* denotes a bonding position;
$P^2$ and $P^2$ are identical or different, and each independently
(1) a hydrogen atom,
(2) an optionally substituted $C_{1-10}$alkyl group,
(3) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group),
(4) an optionally substituted $C_{6-10}$aryl group,
(5) an optionally substituted $C_{1-10}$alkylcarbonyl group,
(6) an optionally substituted $C_{6-10}$arylcarbonyl group, or
(7) an optionally substituted $C_{3-10}$cycloalkyl group; and
wherein
when $P^1$ and $P^2$ are identical or different, and each independently an optionally substituted $C_{1-10}$alkyl group, an optionally substituted $C_{6-10}$aryl group, an optionally substituted $C_{1-10}$alkylcarbonyl group, or an optionally substituted $C_{3-10}$cycloalkyl group, then they may be taken together to form an optionally substituted cyclic ketal, wherein $P^1$ and $P^2$ are not both hydrogen atoms;
$P^3$ is
(1) an optionally substituted $C_{1-10}$alkyl group,
(2) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group),
(3) an optionally substituted 3- to 12-membered monocyclic or polycyclic heterocyclic group (wherein in the heterocyclic group, a carbon atom adjacent to a heteroatom in the ring is bound to the oxygen atom to which $P^3$ in the formula (Yb) is attached),
(4) an optionally substituted $C_{2-10}$alkenyl group,
(5) an optionally substituted $C_{6-10}$aryl group,
(6) an optionally substituted $C_{1-10}$alkylcarbonyl group,
(7) an optionally substituted $C_{6-10}$arylcarbonyl group,
(8) an optionally substituted $C_{1-10}$alkyloxycarbonyl group.

(9) an optionally substituted $C_{6-10}$aryloxycarbonyl group,
(10) an optionally substituted $C_{2-10}$alkenyloxycarbonyl group,
(11) an optionally substituted aminocarbonyl group,
(12) an optionally substituted $C_{1-10}$alkylsulfonyl group,
(13) an optionally substituted $C_{6-10}$arylsulfonyl group, or
(14) a formyl group;
$P^4$ is
(1) an optionally substituted $C_{1-10}$alkyl group,
(2) a silyl group (the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group),
(3) an optionally substituted 3- to 12-membered monocyclic or polycyclic heterocyclic group (wherein in the heterocyclic group, a carbon atom adjacent to a heteroatom in the ring is bound to the oxygen atom to which $P^4$ in the formula (Yc) is attached),
(4) an optionally substituted $C_{2-10}$alkenyl group,
(5) an optionally substituted $C_{6-10}$aryl group,
(6) an optionally substituted $C_{1-10}$alkylcarbonyl group,
(7) an optionally substituted $C_{6-10}$arylcarbonyl group,
(8) an optionally substituted $C_{1-10}$alkyloxycarbonyl group,
(9) an optionally substituted $C_{6-10}$aryloxycarbonyl group,
(10) an optionally substituted $C_{2-10}$alkenyloxycarbonyl group,
(11) an optionally substituted aminocarbonyl group,
(12) an optionally substituted $C_{1-10}$alkylsulfonyl group,
(13) an optionally substituted $C_{6-10}$arylsulfonyl group, or
(14) a formyl group;
$R^2$ is an optionally substituted $C_{1-10}$alkyl group;
$R^3$ is an optionally substituted $C_{1-10}$alkyl group; and
$R^4$ and $R^5$ are identical or different, and each independently a hydrogen atom, or an optionally substituted $C_{1-10}$alkyl group,
with the proviso that 2-(2-methyl-1,3-dioxolane-2-yl)naphtho[2,3-b]furan-4,9-dione and 1-(4,9-dioxo-4,9-dihydronaphtho[2,3-b]furan-2-yl)ethyl acetate are excluded.

[Item 47]

The compound according to item 46, or a tautomer thereof, or an optionally pharmaceutically acceptable salt thereof or solvate thereof, wherein $P^1$ and $P^2$ are identical or different, and each independently
(1) a hydrogen atom,
(2) a $C_{1-6}$alkyl group optionally substituted with one to three groups independently selected from the group consisting of a halogen atom and a $C_{1-6}$alkoxy group,
(3) a silyl group optionally substituted with one to three $C_{1-6}$alkyl groups,
(4) a phenyl group,
(5) a benzyl group, or
(6) a $C_{1-6}$alkylcarbonyl group; or
$P^1$ and $P^2$ are taken together to form a cyclic ketal selected from the group consisting of
(7) 1,3-dioxolane optionally substituted with one to four groups independently selected from the group consisting of a $C_{1-6}$alkyl group, a $C_{1-6}$alkoxy group, a hydroxyl group, and a phenyl group,
(8) 1,3-dioxolane-4-one,
(9) 1,3-dioxolane-4,5-dione,
(10) 1,3-dioxane optionally substituted with one to four groups independently selected from the group consisting of a $C_{1-6}$alkyl group, a $C_{1-6}$alkoxy group, a hydroxyl group, and a phenyl group,
(11) 1,3-dioxane-4-one,
(12) 1,3-dioxane-4,6-dione, and
(13) benzo[d][1,3]dioxole.

[Item 48]

The compound according to item 46 or 47, or a tautomer thereof, or an optionally pharmaceutically acceptable salt thereof or solvate thereof, wherein $P^1$ and $P^2$ are identical or different, and each independently a $C_{1-6}$alkyl group or a $C_{1-6}$alkylcarbonyl group, or $P^1$ and $P^2$ are taken together to form a cyclic ketal selected from the group consisting of 1,3-dioxolane optionally substituted with one to four $C_{1-6}$alkyl groups, and 1,3-dioxane optionally substituted with one to four $C_{1-6}$alkyl groups.

[Item 49]

The compound according to any one of items 46 to 48, or a tautomer thereof, or an optionally pharmaceutically acceptable salt thereof or solvate thereof,
wherein $P^1$ and $P^2$ are identical or different, and each independently a methyl group, an ethyl group, a propyl group, an isopropyl group, a butyl group, a tert-butyl group, a pentyl group, or an acetyl group, or $P^1$ and $P^2$ are taken together to form a cyclic ketal selected from the group consisting of 4-methyl-1,3-dioxolane, 4,5-dimethyl-1,3-dioxolane, 4,4,5,5-tetramethyl-1,3-dioxolane, 1,3-dioxane, 4-methyl-1,3-dioxane, 5-methyl-1,3-dioxane, and 5,5-dimethyl-1,3-dioxane.

[Item 50]

The compound according to any one of items 46 to 49, or a tautomer thereof, or an optionally pharmaceutically acceptable salt thereof or solvate thereof, wherein $P^1$ and $P^2$ are taken together to form 1,3-dioxane.

[Item 51]

The compound according to any one of items 46 to 50, or a tautomer thereof, or an optionally pharmaceutically acceptable salt thereof or solvate thereof, wherein $R^2$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 52]

The compound according to any one of items 46 to 51, or a tautomer thereof, or an optionally pharmaceutically acceptable salt thereof or solvate thereof, wherein $R^2$ is a $C_{1-6}$alkyl group.

[Item 53]

The compound according to any one of items 46 to 52, or a tautomer thereof, or an optionally pharmaceutically acceptable salt thereof or solvate thereof, wherein $R^2$ is a methyl group.

[Item 54]

The compound according to any one of items 46 to 53, or a tautomer thereof, or an optionally pharmaceutically acceptable salt thereof or solvate thereof, wherein $P^3$ is
(1) a $C_{1-6}$alkyl group (the alkyl group is optionally substituted with one to three groups independently selected from the group consisting of
  (a) a halogen atom,
  (b) a $C_{1-6}$alkoxy group,
  (c) a silyloxy group substituted with three substituents independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group);

(2) a silyl group substituted with three substituents independently selected from the group consisting of a $C_{1-6}$alkyl group and a phenyl group;
(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^3$ in the formula (Yb) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{1-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups); or
(14) a formyl group.

[Item 55]
The compound according to any one of items 46 to 54, or a tautomer thereof, or an optionally pharmaceutically acceptable salt thereof or solvate thereof, wherein $P^3$ is
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group.
(3) a trityl group,
(4) a silyl group substituted with three substituents independently selected from the group consisting of a $C_{1-6}$ alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group, or
(10) an allyloxycarbonyl group.

[Item 56]
The compound according to any one of items 46 to 55, or a tautomer thereof, or an optionally pharmaceutically acceptable salt thereof or solvate thereof, wherein $P^3$ is
(1) a $C_{1-6}$alkyl group optionally substituted with one to three $C_{1-6}$alkoxy groups;
(2) a silyl group substituted with three substituents independently selected from the group consisting of a $C_{1-6}$alkyl group and a phenyl group; or
(3) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached).

[Item 57]
The compound according to any one of items 46 to 56, or a tautomer thereof, or an optionally pharmaceutically acceptable salt thereof or solvate thereof, wherein $P^3$ is a methoxymethyl group, a tert-butyl group, a 1-ethoxyethyl group, a 2-tetrahydropyranyl group, a 2-tetrahydrofuranyl group, a trimethylsilyl group, a triethylsilyl group, or a tert-butyldimethylsilyl group.

[Item 58]
The compound according to any one of items 46 to 57, or a tautomer thereof, or an optionally pharmaceutically acceptable salt thereof or solvate thereof, wherein $P^3$ is a 2-tetrahydropyranyl group, a trimethylsilyl group, or a tert-butyldimethylsilyl group.

[Item 59]
The compound according to any one of items 46 to 58, or a tautomer thereof, or an optionally pharmaceutically acceptable salt thereof or solvate thereof, wherein $R^3$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 60]
The compound according to any one of items 46 to 59, or a tautomer thereof, or an optionally pharmaceutically acceptable salt thereof or solvate thereof, wherein $R^3$ is a $C_{1-6}$alkyl group.

[Item 61]
The compound according to any one of items 46 to 60, or a tautomer thereof, or an optionally pharmaceutically acceptable salt thereof or solvate thereof, wherein $R^3$ is a methyl group.

[Item 62]
The compound according to any one of items 46 to 61, or a tautomer thereof, or an optionally pharmaceutically acceptable salt thereof or solvate thereof, wherein $P^4$ is
(1) a $C_{1-6}$alkyl group (the alkyl group is optionally substituted with one to three groups independently selected from the group consisting of
  (a) a halogen atom,
  (b) a $C_{1-6}$alkoxy group,
  (c) a silyloxy group substituted with three groups independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group);
(2) a silyl group substituted with three substituents independently selected from the group consisting of a $C_{1-6}$alkyl group and a phenyl group;

(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^4$ in the formula (Yc) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{2-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups); or
(14) a formyl group.

[Item 63]
The compound according to any one of items 46 to 62, or a tautomer thereof, or an optionally pharmaceutically acceptable salt thereof or solvate thereof, wherein $P^4$ is
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^4$ in the formula (Yc) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group, or
(10) an allyloxycarbonyl group.

[Item 64]
The compound according to any one of items 46 to 63, or a tautomer thereof, or an optionally pharmaceutically acceptable salt thereof or solvate thereof, wherein $P^4$ is
(1) a $C_{1-6}$alkyl group optionally substituted with one to three $C_{1-6}$alkoxy groups;
(2) a silyl group substituted with three substituents independently selected from the group consisting of a $C_{1-6}$alkyl group and a phenyl group; or
(3) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^4$ in the formula (Yc) is attached).

[Item 65]
The compound according to any one of items 46 to 64, or a tautomer thereof, or an optionally pharmaceutically acceptable salt thereof or solvate thereof, wherein $P^4$ is a methoxymethyl group, a tert-butyl group, a 1-ethoxyethyl group, a 2-tetrahydropyranyl group, a 2-tetrahydrofuranyl group, a trimethylsilyl group, a triethylsilyl group, or a tert-butyldimethylsilyl group.

[Item 66]
The compound according to any one of items 46 to 65, or a tautomer thereof, or an optionally pharmaceutically acceptable salt thereof or solvate thereof, wherein $P^4$ is a 2-tetrahydropyranyl group, a trimethylsilyl group, or a tert-butyldimethylsilyl group.

[Item 67]
The compound according to any one of items 46 to 66, or a tautomer thereof, or an optionally pharmaceutically acceptable salt thereof or solvate thereof, wherein $R^4$ and $R^5$ are identical or different, and each independently
(1) a hydrogen atom, or
(2) a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

[Item 68]
The compound according to any one of items 46 to 67, or a tautomer thereof, or an optionally pharmaceutically acceptable salt thereof or solvate thereof, wherein $R^4$ and $R^5$ are identical or different, and each independently
(1) a hydrogen atom, or
(2) a $C_{1-6}$alkyl group.

[Item 69]
The compound according to any one of items 46 to 68, or a tautomer thereof, or an optionally pharmaceutically acceptable salt thereof or solvate thereof, wherein $R^4$ and $R^5$ are hydrogen atoms.

[Item 70]
The compound according to items 46 to 61, or a tautomer thereof, or an optionally pharmaceutically acceptable salt thereof or solvate thereof, wherein Y is a group represented by the formula (Ya) or (Yb).

[Item 71]
The compound according to item 46, or a tautomer thereof, or an optionally pharmaceutically acceptable salt thereof or solvate thereof, wherein Y is a group represented by the formula (Ya) or (Yb), wherein
$P^1$ and $P^2$ are taken together to form a cyclic ketal selected from the group consisting of 1,3-dioxolane optionally substituted with one to four $C_{1-6}$alkyl groups, and 1,3-dioxane optionally substituted with one to four $C_{1-6}$alkyl groups;
$R^2$ is a $C_{1-6}$alkyl group;
$P^3$ is
(1) a silyl group substituted with three substituents independently selected from the group consisting of a $C_{1-6}$alkyl group and a phenyl group, or (2) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached); and $R^3$ is a $C_{1-6}$alkyl group.

[Item 72]

The compound according to any one of items 46 to 53 and 71, or a tautomer thereof, or an optionally pharmaceutically acceptable salt thereof or solvate thereof, wherein Y is a group represented by the formula (Ya).

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

According to the production method of the present invention, naphtho[2,3-b]furan-4,9-dione with a substitution at position 2 can be produced more safely, at a higher yield, and with higher purity compared to known production methods. Thus, substances related to the production of 2-alkylcarbonylnaphtho[2,3-b]furan-4,9-dione that are useful as a pharmaceutical product can be produced safely and at low cost.

The present invention also provides a method, which has a higher yield when constructing a naphtho[2,3-b]furan-4,9-dione backbone with a substitution at position 2, produces a product of interest more efficiently, and is more industrially suitable, compared to the known production methods described in the prior art documents.

The method of the present invention can obtain 2-acetylnaphtho[2,3-b]furan-4,9-dione at a high yield without generating 2-acetyl-2,3-dihydronaphtho[2,3-b]furan-4,9-dione.

The method of the present invention has excellent reaction efficiency, as only 1.0 to 1.5 equivalents of acetylene compound needs to be used with respect to the substrate when constructing a naphtho[2,3-b]furan-4,9-dione backbone with a substitution at position 2. The product has excellent stability, and the reaction yield is also high. In addition, residual palladium in pharmaceutical products would not be an issue because a palladium catalyst is not used.

Since the reaction of the present invention does not need to use copper acetylide by first isolating it, an advantage of being able to readily perform a reaction operation and the like can also be provided.

DESCRIPTION OF EMBODIMENTS

The present invention is explained hereinafter while showing the best mode of the invention. Throughout the entire specification, a singular expression should also be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

In the present specification, the presence of the following tautomers can be considered for a carbonyl group and hydroxyl group of a compound represented by formula (1) and an optionally pharmaceutically acceptable salt thereof. The optimal tautomer can vary depending on the type of substituent X, but all isomers are represented with formula (1) for convenience's sake.

[Chemical formula 17]

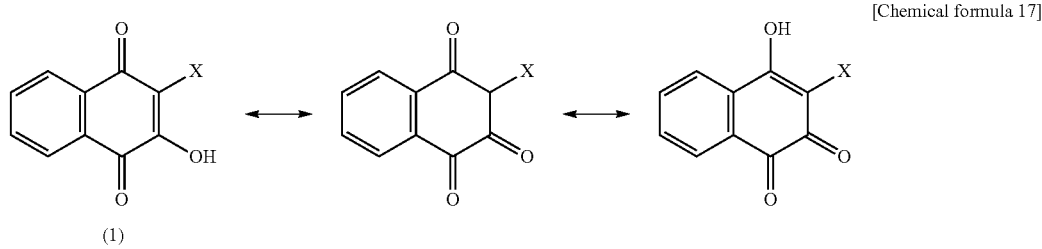

(1)

For the compounds of the present invention, the presence of tautomers can also be considered in some cases in compounds of other formulas (e.g., formula (I)) in addition to the above. For example, it is understood that more tautomers can be appropriately considered depending on the substituent. It is understood that the present invention encompasses any such tautomers.

The compounds of the present invention may be in a form of a solvate (e.g., hydrate). Thus, the compounds of the present invention also encompass compounds represented by formula (I) or a tautomer thereof, or an optionally pharmaceutically acceptable salt thereof or solvate thereof (e.g., hydrate).

The compounds represented by formula (I) may have one or in some cases more asymmetric carbon atoms, or geometric isomerism or axial chirality, so that the compounds may be present as several types of stereoisomers. In the present invention, such stereoisomers and mixtures and racemates thereof are also encompassed by the compounds of the present invention.

A deuterated form in which any one or more $^1$H (hydrogen atom) of a compound represented by formula (I) has been converted to $^2$H (D: deuterium atom) is also encompassed by the compound represented by formula (I).

Compounds represented by formula (I) or tautomers thereof, or optionally pharmaceutically acceptable salts thereof obtained as a crystal may be present as crystalline polymorphism. The compounds of the present invention include all crystalline forms.

The number of carbons in the definition of a "substituent" may be expressed herein as, for example, "$C_{1-6}$" or the like. Specifically, the expression "$C_{1-6}$alkyl" is synonymous with an alkyl group having 1 to 6 carbons. As used herein, a substituent with no explicit description of the particular terms "may have a substitution", "optionally substituted", or "substituted" refers to an "unsubstituted" substituent. For example, a "$C_{1-6}$alkyl" means that the substituent is "unsubstituted".

As used herein, the term "group" refers to a monovalent group. For example, an "alkyl group" refers to a monovalent saturated hydrocarbon group. The term "group" may be also omitted in the explanation of a substituent in the present specification.

The terms used herein are explained hereinafter.

The number of substituents in a group defined by "may have a substitution", "optionally substituted", or "substituted" is not particularly limited, as long as a substitution is possible. The number of substituents is 0, 1, or multiple substituents. Moreover, unless otherwise indicated, the description for each group is also applicable when the group is a part or a substituent of other groups.

As used herein, examples of a "halogen atom" include a fluorine atom, a chlorine atom, a bromine atom, an iodine atom, and the like. A halogen atom is preferably a bromine atom or an iodine atom, and more preferably a bromine atom.

An "alkyl group" refers to a linear or branched, saturated hydrocarbon group. For example, a "$C_{1-4}$alkyl group" or a "$C_6$alkyl group" refers to an alkyl group having one to four or six carbon atoms. The same applies to description with other numbers. A "$C_{1-10}$alkyl group" is preferably a "$C_{1-6}$alkyl group" and more preferably a "$C_{1-4}$alkyl group". Specific examples of the "$C_{1-10}$alkyl group" include a methyl group, an ethyl group, a propyl group, a 1-methylethyl group, a butyl group, a 2-methylpropyl group, a 1-methylpropyl group, a 1,1-dimethylethyl group, a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a hexyl group, a heptyl group, an octyl group, a nonyl group, a decyl group, and the like. Specific examples of the "$C_{1-6}$alkyl group" include examples of those having one to six carbon atoms in the specific examples of the "$C_{1-10}$alkyl group". Specific examples of the "$C_{1-4}$alkyl group" include examples of those having one to four carbon atoms in the specific examples of the "$C_{1-10}$alkyl group".

A "$C_{3-10}$cycloalkyl group" refers to a cyclic alkyl having three to ten carbon atoms, including cyclic alkyl having a partially bridged structure. The "$C_{3-10}$cycloalkyl group" is preferably a "$C_{3-7}$cycloalkyl group" and more preferably a "$C_{4-6}$cycloalkyl group". Specific examples of the "$C_{3-10}$cycloalkyl group" include a cyclopropyl group, a cyclobutyl group, a cyclopentyl group, a cyclohexyl group, a cycloheptyl group, a cyclooctyl group, an adamantyl group, and the like. Specific examples of the "$C_{3-7}$cycloalkyl group" include a cyclopropyl group, a cyclobutyl group, a cyclopentyl group, a cyclohexyl group, a cycloheptyl group, and the like.

A "$C_{2-10}$alkenyl group" refers to a linear or branched, unsaturated hydrocarbon group having two to ten carbon atoms and containing one to five double bonds. A "$C_{2-10}$alkenyl group" is preferably a "$C_{2-6}$alkenyl group". Specific examples of the "$C_{2-10}$alkenyl group" include a vinyl group, 1-propenyl group, a 2-propenyl group (allyl group), a 2-methyl-2-propenyl group, a 2-butenyl group, a 1,3-butanedienyl group, a 3-methyl-2-butenyl group, a 2-pentenyl group, a 2-hexenyl group, a 1,3,5-hexanetrienyl group, a 2-heptenyl group, a 2-octenyl group, a 2-nonenyl group, a 2-decenyl group, and the like. Specific examples of "$C_{2-6}$alkenyl group" include examples with 2 to 6 carbons in the specific examples of "$C_{2-10}$alkenyl group".

A "$C_{1-10}$alkoxy group" refers to a "$C_{1-10}$alkyloxy group", and the "$C_{1-10}$alkyl" moiety is defined the same as the "$C_{1-10}$alkyl group". The "$C_{1-10}$alkoxy group" is preferably a "$C_{1-6}$alkoxy group" and more preferably a "$C_{1-4}$alkoxy group". Specific examples of the "$C_{1-10}$alkoxy group" include a methoxy group, an ethoxy group, a propoxy group, a 1-methylethoxy group, a butoxy group, a 2-methylpropoxy group, a 1-methylpropoxy group, a 1,1-dimethylethoxy group, a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, and the like.

A "$C_{6-10}$aryl group" refers to an aromatic hydrocarbon having six to ten carbon atoms. Specific examples of the "$C_{6-10}$aryl group" include a phenyl group, a 1-naphthyl group, a 2-naphthyl group, and the like. A phenyl group is particularly preferable.

The "$C_{6-10}$aryl" moiety of the "$C_{6-10}$aryloxy group" is defined the same as the "$C_{6-10}$aryl group". $C_{6-10}$aryloxy groups are preferably a phenoxy group.

The "$C_{1-10}$alkyl" moiety of the "$C_{1-10}$alkylcarbonyl group" is defined the same as the "$C_{1-10}$alkyl group". The "$C_{1-10}$alkylcarbonyl group" is preferably a "$C_{1-6}$alkylcarbonyl group". Specific examples of "$C_{1-6}$alkylcarbonyl group" include a methylcarbonyl group (acetyl group), an ethylcarbonyl group, a propylcarbonyl group, a 1-methylethylcarbonyl group, a butylcarbonyl group, a 2-methylpropylcarbonyl group, a 1-methylpropylcarbonyl group, a 1,1-dimethylethylcarbonyl group, and the like.

The "$C_{6-10}$aryl" moiety of the "$C_{6-10}$arylcarbonyl group" is defined the same as the "$C_{6-10}$aryl group". Specific examples of the "$C_{6-10}$arylcarbonyl group" include a phenylcarbonyl group, a 1-naphthylcarbonyl group, a 2-naphthylcarbonyl group, and the like. It is preferably a phenylcarbonyl group.

The "$C_{1-10}$alkyloxy" moiety of the "$C_{1-10}$alkyloxycarbonyl group" is defined the same as the "$C_{1-10}$alkoxy group". The "$C_{1-10}$alkyloxycarbonyl group" is preferably a "$C_{1-6}$ alkyloxycarbonyl group". Specific examples of "$C_{1-6}$alkyloxycarbonyl group" include a methoxycarbonyl group, an ethoxycarbonyl group, a propoxycarbonyl group, a 1-methylethoxycarbonyl group, a butoxycarbonyl group, a 2-methylpropoxycarbonyl group, a 1-methylpropoxycarbonyl group, a 1,1-dimethylethoxycarbonyl group, a pentyloxycarbonyl group, 3-methylbutoxycarbonyl group, a 2-methylbutoxycarbonyl group, a 2,2-dimethylpropoxycarbonyl group, a 1-ethylpropoxycarbonyl group, a 1,1-dimethylpropoxycarbonyl group, a hexyloxycarbonyl group, a 4-methylpentyloxycarbonyl group, a 3-methylpentyloxycarbonyl group, a 2-methylpentyloxycarbonyl, a 1-methylpentyloxycarbonyl group, a 3,3-dimethylbutoxycarbonyl group, a 2,2-dimethylbutoxycarbonyl group, a 1,1-dimethylbutoxycarbonyl, a 1,2-dimethylbutoxycarbonyl group, and the like.

The "C$_{6-10}$aryloxy" moiety of the "C$_{6-10}$aryloxycarbonyl group" is defined the same as the "C$_{6-10}$aryloxy group". The "C$_{6-10}$aryloxycarbonyl group" is preferably phenoxycarbonyl.

The "C$_{2-10}$alkenyl" moiety of the "C$_{2-10}$alkenyloxycarbonyl group" is defined the same as the "C$_{2-10}$alkenyl group". The "C$_{1-10}$alkenyloxycarbonyl group" is preferably a "C$_{2-6}$alkenyloxycarbonyl group". Specific examples of "C$_{2-6}$alkenyloxycarbonyl group" include allyloxycarbonyl.

A "silyl group" refers to a substituent that binds to a silicon atom. A "silyl group substituted with three substituents independently selected from the group consisting of a C$_{1-10}$alkyl group, a C$_{1-10}$alkoxy group and a C$_{6-10}$aryl group" means that a total of three substituents independently selected from the group consisting of a "C$_{1-10}$ alkyl group", a "C$_{1-10}$alkoxy group", and a "C$_{6-10}$aryl group" are bound to a silicon atom. Specific examples of "silyl group substituted with three substituents independently selected from the group consisting of a C$_{1-10}$alkyl group, a C$_{1-10}$alkoxy group, and a C$_{6-10}$aryl group" include a trimethylsilyl group, a tert-butylmethoxyphenylsilyl group, a triethylsilyl group, a tert-butyldimethylsilyl group, a triisopropylsilyl group, and a tert-butyldiphenylsilyl group. It is preferably a trimethylsilyl group, a triethylsilyl group, or a tert-butyldimethylsilyl group, and more preferably a trimethylsilyl group.

The "silyl" moiety of the "silyloxy group" is defined the same as the "silyl group". Specific examples of "silyloxy group substituted with three groups independently selected from the group consisting of a C$_{1-6}$alkyl group and a phenyl group" include a trimethylsilyloxy group, a triethylsilyloxy group, a tert-butyldimethylsilyloxy group, a triisopropylsilyloxy group, and a tert-butyldiphenylsilyloxy group. It is preferably a trimethylsilyloxy group, a triethylsilyloxy group, or a tert-butyldimethylsilyloxy group, and more preferably a trimethylsilyloxy group.

A "cyclic ketal" refers to a ring having two or more oxygen atoms therein, which are bound to a carbon atom in the same ring. A cyclic ketal can be obtained by fusing diol, dicarboxylic acid, hydroxycarboxylic acid, catechol, or the like with ketone. Specific examples of cyclic ketals include, as shown in the following formulas, 1,3-dioxolane, 4-methyl-1,3-dioxolane, 4,5-dimethyl-1,3-dioxolane, 4,4,5,5-tetramethyl-1,3-dioxolane, 1,3-dioxolane-4-one, 1,3-dioxolane-4,5-dione, benzo[d][1,3]dioxole, 4-phenyl-1,3-dioxolane, 4,5-diphenyl-1,3-dioxolane, [1,3]dioxolo[4,5-b]pyridine, 4-pyridyl-1,3-dioxolane, 1,3-dioxane, 4-methyl-1,3-dioxane, 5-methyl-1,3-dioxane, 5,5-dimethyl-1,3-dioxane, 1,3-dioxane-4-one, 1,3-dioxane-4,6-dione, and 1,5-dihydro-3H-2,4-benzodioxepin. It is preferably 1,3-dioxolane, 4-methyl-1,3-dioxolane, 4,5-dimethyl-1,3-dioxolane, 4,4,5,5-tetramethyl-1,3-dioxolane, 1,3-dioxolane-4-one, 1,3-dioxolane-4,5-dione, 1,3-dioxane, 4-methyl-1,3-dioxane, 1,3-dioxane-4-one, or 1,3-dioxane-4,6-dione, more preferably 1,3-dioxolane, 4-methyl-1,3-dioxolane, 4,5-dimethyl-1,3-dioxolane, 4,4,5,5-tetramethyl-1,3-dioxolane, 1,3-dioxane, or 4-methyl-1,3-dioxane, and most preferably 1,3-dioxolane or 1,3-dioxane.

{Chemical formula 18}

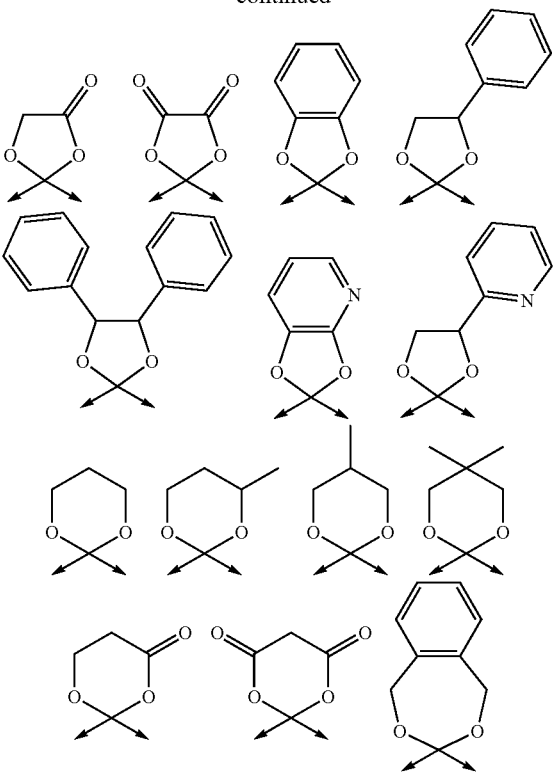

Examples of "3- to 12-membered monocyclic or polycyclic heterocyclic group" include monocyclic or polycyclic heterocyclic groups including one to four atoms independent selected from the group consisting of a nitrogen atom, an oxygen atom, and a sulfur atom. It is preferably a 3- to 10-membered group, more preferably a 3- to 8-membered group, and still more preferably 5- or 6-membered group. Each of the nitrogen atom, oxygen atom, and sulfur atom is an atom constituting a ring. The heterocyclic group may be either saturated or partially unsaturated. A saturated heterocyclic group is preferred. Specific examples of "heterocyclic group" include an oxiranyl group, an aziridinyl group, an azetidinyl group, a pyranyl group, a tetrahydrofuranyl group, a pyrrolidinyl group, an imidazolidinyl group, a piperidinyl group, a piperadinyl group, a morpholinyl group, a thiomorpholinyl group, a dioxothiomorpholinyl group, a hexamethyleneiminyl group, an oxazolidinyl group, a thiazolidinyl group, an imidazolidinyl group, an oxoimidazolidinyl group, a dioxoimidazolidinyl group, an oxooxazolidinyl group, a dioxooxazolidinyl group, a dioxothiazolidinyl group, a tetrahydropyridyl group, an oxetanyl group, a dioxanyl group, a tetrahydrothiopyranyl group, a tetrahydropyranyl group, and the like. It should be noted that the group also encompasses a heterocyclic group having a bridged structure. For such a group, a nitrogen atom constituting the ring cannot be at a position to be attached in "the group". In other words, the group does not encompass the concepts of, for example, a 1-pyrrolidino group and the like.

An "aminocarbonyl group" refers to a group in which an "amino group" is bound to a carbonyl group. As used herein, the "amino" refers to, with respect to a nitrogen atom, unsubstituted amino, mono-substituted amino, di-substituted amino, or 3- to 12-membered cyclic amino. Specific examples thereof include a methylaminocarbonyl group, a cyclopropylaminocarbonyl group, a dimethylaminocarbonyl group, a dicyclopropyl aminocarbonyl group, a phenylaminocarbonyl group and the like. It is preferably a phenylaminocarbonyl group.

The "$C_{1-10}$alkyl" moiety of the "$C_{1-10}$alkylsulfonyl group" is defined the same as the "$C_{1-10}$alkyl group". "$C_{1-10}$alkylsulfonyl group" is preferably a "$C_{1-6}$alkylsulfonyl group". Specific examples of "$C_{1-6}$alkylsulfonyl group" include a methanesulfonyl group, an ethanesulfonyl group, a propanesulfonyl group, a 1-methylethanesulfonyl group, a butanesulfonyl group, a 2-methylpropanesulfonyl group, a 1-methylpropanesulfonyl group, a 1,1-dimethylethanesulfonyl group, and the like.

The "$C_{6-10}$aryl" moiety of the "$C_{6-10}$arylsulfonyl group" is defined the same as the "$C_{6-10}$aryl group". "$C_{6-10}$arylsulfonyl group" is preferably a "$C_6$arylsulfonyl group" Specific examples of the "$C_6$arylsulfonyl group" include a benzensulfonyl group (the benzenfulfonyl group is defined the same as a phenylsulfonyl group), a p-toluenesulfonyl group, and the like.

For a "protecting group", conversion of a certain functional group to a functional group that is inactive in a reaction when a compound with the certain functional group induces decomposition or side effects due to the functional group in the reaction or a delay in reaction or the like is referred to as "protection", and said inactive functional group is referred to as a protecting group. Protection presumes that a functional group is returned to the original functional group by a few steps of chemical conversion, or is converted to another desirable functional group.

Specific examples of "protecting group" are described in documents such as Wuts, P. G. M.; Greene, T. W. Protective Groups in Organic Synthesis, 5th ed., WILEY, 2014 with methods of introducing and removing a protecting group.

Specific examples of "protecting group for a carbonyl group" include, but are not limited to, dimethyl ketal, ethylmethyl ketal, diethyl ketal, di(2-chloroethyl)ketal, bis(2,2,2-trichloroethyl)ketal, dipropyl ketal, diisopropyl ketal, dibutyl ketal, di-tert-butyl ketal, dipentyl ketal, ditrimethylsilyl ketal, dibenzyl ketal, diacetyl ketal, 4-methyl-1,3-dioxolane, 4,5-dimethyl-1,3-dioxolane, 4,4,5,5-tetramethyl-1,3-dioxolane, 4,5-diphenyl-1,3-dioxolane, 1,3-dioxolane, 1,3-dioxalane-4-one, 1,3-dioxolane-4,5-dione, benzo[d][1,3]dioxole, 1,5-dihydro-3H-2,4-benzodioxepin, 1,3-dioxane, 1,3-dioxane-4-one, 1,3-dioxane-4,6-dione, 4-methyl-1,3-dioxane, acetyl enol ester, tert-butyldimethylsilyl enol ether, and trimethylsilyl enol ether.

Protecting groups for a carbonyl group are preferably dimethyl ketal, diethyl ketal, dibenzyl ketal, diacetyl ketal, 4-methyl-1,3-dioxolane, 4,5-dimethyl-1,3-dioxolane, 1,3-dioxolane, or 1,3-dioxane.

Protecting groups for a carbonyl group are more preferably 1,3-dioxolane, 4-methyl-1,3-dioxolane, 4,5-dimethyl-1,3-dioxolane, or 1,3-dioxane.

Protecting groups for a carbonyl group are most preferably 1,3-dioxolane or 1,3-dioxane.

Specific examples of a "protecting group for a hydroxyl group" include, but are not limited to, ether protecting groups for methyl ether, methoxymethyl ether, ethyl ether, allyl ether, tert-butyl ether, 1-ethoxyethyl ether, 2-tetrahydropyranyl ether, 2-tetrahydrofuranyl ether, benzyl ether, phenyl ether, tert-butyldimethylsilyl ether, triethylsilyl ether, trimethylsilyl ether, and the like, ester protecting groups for formyl ester, acetyl ester, propionyl ester, trifluoroacetyl ester, benzoyl ester, 2,2,2-trichloroethylcarbonyl ester, benzyloxycarbonyl ester, allyloxycarbonyl ester, tert-butyloxycarbonyl ester, phenylcarbamate ester, dimethylcarbamate ester, methanesulfonate ester, and p-toluenesulfonic acid ester.

"Leaving group" is an atomic group, which is bound by a chemical bond that is more readily cleaved compared to other chemical bonds in the molecule in a reaction, and becomes an anion or a neutral molecule after cleavage. Specific examples of a "leaving group" include, but are not limited to, a fluorine atom, a chlorine atom, a bromine atom, an iodine atom, phenyliodonio, a methanesufonyloxy group, a p-toluenesulfonyloxy group, a trifluoromethanesufonyloxy group and the like. A leaving group is preferably a bromine atom, an iodine atom, or phenyliodonio, more preferably a bromine atom or an iodine atom, and most preferably a bromine atom.

The "metal compound" in "metal or a metal compound" encompasses both organic and inorganic metal compounds. Complexes in which water, alcohol, ketone, ammonia, amine compound, cyanide ion, halogen, phosphine compound, thiophene, thiol, or another coordinated compound has a coordinate bond with a metal atom are encompassed thereby.

Specific examples of a "metal compound" include copper compounds, palladium compounds, tin compounds, zinc compounds, nickel compounds, lithium compounds, magnesium compounds, aluminum compounds, boron compounds, silicon compounds and mixtures thereof. The "metal compound" is preferably a copper compound, a palladium compound, a zinc compound, or a nickel compound, more preferably a copper compound or a palladium compound, and still more preferably a copper compound. When a mixture of metals or metal compounds is used, the order of adding metals or metal compounds are appropriately adjusted.

Specific examples of "metal" include metal copper, metal palladium, metal tin, metal zinc, metal nickel, metal lithium, metal magnesium, metal aluminum, boron, silicon, and mixtures thereof (alloy and the like). The "metal" is preferably metal copper, metal palladium, metal zinc, or metal nickel, more preferably metal copper or metal palladium, and still more preferably metal copper.

Specific examples of "metal copper or a copper compound" include, but are not limited to, metal copper (0), copper(I) acetate, copper(II) acetate, copper(I) oxide, copper (II) oxide, copper(I) chloride, copper(II) chloride, copper(I) bromide, copper(II) bromide, copper(I) iodide, copper(II) iodide, copper(II) acetylacetonate, copper(I) cyanide, copper(II) fluoride, copper(I) trifluoromethanesulfonate, a mixture thereof and the like. Metal copper or a copper compound is preferably metal copper (0), copper(I) bromide, copper(I) acetate, copper(I) oxide, or copper(II) oxide, more preferably metal copper (0) or copper(I) oxide, and most preferably copper(I) oxide. Metal copper (0) with a small particle size is desirable for use. Metal copper (0) that is pulverized, metal copper manufactured by atomization, electrical explosion, laser synthesis or the like, metal copper prepared by reducing a monovalent or divalent copper salt, sponge copper, copper-bearing carbon or the like can be used.

A "palladium compound" refers to a compound comprising palladium. Specific examples of "metal palladium or a palladium compound" include, but are not limited to, metal palladium (0), palladium on carbon, palladium(II) acetate, tetrakis triphenylphosphine palladium (0), and dichlorotris triphenylphosphine palladium (II).

In the reaction of the present invention, a phase transfer catalyst such as tetrabutylammonium hydroxide, a phosphine compound such as triphenylphosphine, a nitrogen compound such as 1,10-phenanthroline, bipyridyl, or tetramethylethylenediamine, or a compound with a property to have a coordinate bond with metal may be added as needed to the extent the reaction is not negatively affected.

A "base" encompasses both organic bases and inorganic bases.

Specific examples of the "organic base" include triethylamine, N,N,N',N'-tetramethylethane-1,2-diamine, N,N-dimethylaniline, N,N-diisopropylethylamine, N-methylpyrrolidine, N-methylpiperidine, 1,4-diazabicyclo[2.2.2]octane. N-methylmorpholine, diazabicycloundecene, methylamine, diisopropylamine, pyrimidine, and pyridine. An organic base is more preferably triethylamine, diisopropylethylamine N,N,N',N'-tetramethylethane-1,2-diamine, 1,4-diazabicyclo[2.2.2]octane, N-methylpiperidine, pyrimidine, and pyridine, still more preferably N,N,N',N'-tetramethylethane-1,2-diamine, 1,4-diazabicyclo[2.2.2]octane, N-methylpiperidine, pyrimidine, and pyridine, and most preferably pyridine.

Specific examples of the "inorganic base" include, but are not limited to, ammonia, lithium hydroxide, sodium hydroxide, calcium hydroxide, barium hydroxide, sodium carbonate, sodium hydrogen carbonate, potassium carbonate, cesium carbonate, mixtures thereof, and the like. The inorganic base is preferably lithium hydroxide, sodium hydroxide, sodium carbonate, potassium carbonate, or cesium carbonate, more preferably sodium carbonate, potassium carbonate, or cesium carbonate, and most preferably potassium carbonate or cesium carbonate.

A "basic solvent" refers to a solvent exhibiting base properties. Examples of "basic solvent" include an "amine-based solvent" and a solvent prepared by dissolving an "organic base" or "inorganic base" into water or an organic solvent. Specific examples of "basic solvent" include, but are not limited to, aqueous sodium hydroxide solution, aqueous sodium bicarbonate solution, aqueous potassium hydroxide solution, aqueous calcium hydroxide solution, ammonia water, aqueous methylamine solution, toluene solution of triethylamine, pyridine, or pyridine, mixtures thereof, and the like.

An "amine-based solvent" refers to a solvent, which is a compound comprising one or more nitrogen atoms exhibiting basic properties in a molecule and is a solution at a reaction temperature, having a property of dissolving or dispersing a reactant.

Specific examples of the "amine-based solvent" include, but are not limited to, N-methylpiperidine, N,N,N',N'-tetramethylethane-1,2-diamine, N,N-dimethylaniline, N,N-diisopropylethylamine, N-methylpyrrolidine, pyridine, 2-picoline, 3-picoline, 4-picoline, 2,3-lutidine, 2,4-lutidine, 2,6-lutidine, 3,5-lutidine, 2,4,6-collidine, 2-ethylpyridine, 2-hydroxymethylpyridine, pyrazine, pyrimidine, pyridazine, a mixture thereof and the like. An amine-based solvent is preferably N-methylpiperidine, pyridine, 3-picoline, 4-picoline, or pyrimidine, more preferably N-methylpiperidine, pyridine, or 4-picoline, still more preferably N-methylpiperidine or pyridine, and the most preferably pyridine.

"Non-amine-based solvent" refers to a solvent that is not an amine-based solvent. Representative examples of non-amine-based solvents include, but are not limited to, alcohol-based solvents, ketone-based solvents, halogen-based solvents, amide-based solvents, nitrile-based solvents, sulfoxide-based solvents, ether-based solvents, ester-based solvents, hydrocarbon-based solvents, mixtures thereof, and the like.

Specific examples of non-amine-based solvents include, but are not limited to, methanol, ethanol, 1-propanol, 2-propanol, n-butyl alcohol or isobutyl alcohol, ethylene glycol, pentafluoroethanol, chloroform, dichloromethane, carbon tetrachloride, monochlorobenzene, N,N-dimethylacetamide, N,N-dimethylformamide, N-methyl-2-pyrrolidone, acetonitrile, propionitrile, dimethylsulfoxide, diethylsufoxide, diisopropyl ether, tert-butylmethyl ether, cyclopentylethyl ether, cyclopentylmethyl ether, tetrahydrofuran, 2-methyltetrahydrofuran, 1,4-dioxane, anisole, methyl acetate, ethyl acetate, propyl acetate, butyl acetate, toluene, xylene, acetone, methyl ethyl ketone, methyl isobutyl ketone, mixtures thereof, and the like.

As used herein, it is understood that the expression of "at least one independently selected from . . . " as an expression for a solvent or the like encompasses a mixture of two or more options when two or more are selected from the options.

As used herein, the term "pharmaceutically acceptable salt" refers to a salt prepared from a pharmaceutically acceptable and nontoxic acid (including inorganic and organic acids) unless specifically noted otherwise. In addition, "optionally pharmaceutically acceptable salt (thereof)" means that this can be a salt which is discretionally pharmaceutically acceptable. For example, this means that a salt which is not pharmaceutically acceptable can be used up to a certain stage for the production of an intermediate. Examples of pharmaceutically acceptable salts include, but are not limited to, acetic acid, alginic acid, anthranilic acid, benzenesulfonic acid, benzoic acid, camphorsulfonic acid, citric acid, ethenesulfonic acid, formic acid, fumaric acid, furoic acid, gluconic acid, glutamic acid, glucorenic acid, galacturonic acid, glycidic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phenylacetic acid, propionic acid, phosphoric acid, salicylic acid, stearic acid, succinic acid, sulfanilic acid, sulfuric acid, tartaric acid, p-toluenesulfonic acid, and the like.

As used herein, a substituent in "optionally substituted . . . " can be appropriately selected depending on the substituted group. For example, "optionally substituted $C_{1-10}$alkyl group" refers to the $C_{1-10}$alkyl group that is optionally substituted at any replaceable position with a fluorine atom, chlorine atom, methoxy group, or hydroxyl group. Examples thereof include a methyl group, an ethyl group, an n-propyl group, an isopropyl group, a difluoromethyl group, a trifluoromethyl group, a 2-fluoroethyl group, a 2-methoxyethyl group, and the like. It is preferably a methyl group, an ethyl group, a difluoromethyl group, a trifluoromethyl group, a 2-fluoroethyl group, or a 2-methoxyethyl group.

Examples of substituents in "optionally substituted $C_{1-10}$alkoxy group", "optionally substituted $C_{6-10}$aryl group", "optionally substituted $C_{1-10}$alkylcarbonyl group", "optionally substituted $C_{1-10}$alkyloxycarbonyl group", "optionally substituted $C_{6-10}$arylcarbonyl group", "optionally substituted $C_{3-10}$cycloalkyl group", "optionally substituted cyclic ketal", "optionally substituted 1,3-dioxolane", "optionally substituted 3- to 12-membered monocyclic or polycyclic heterocyclic group", "optionally substituted $C_{2-10}$alkenyl group", "optionally substituted $C_{2-10}$alkenyloxycarbonyl group", "optionally substituted aminocarbonyl group", "optionally substituted $C_{1-10}$alkylsulfonyl group", "optionally substituted $C_{6-10}$arylsulfonyl group", "optionally substituted aminocarbonyl group", "optionally substituted phenyl group" "optionally substituted iodonio group", "optimally substituted sulfonyloxy group", or "optionally substituted phosphoryloxy group" include substitutes selected from the group of the following substituent group (α). These substituents can replace one or more at any replaceable position.

Substituents (α): halogen atom, cyano group, nitro group, amino group, methylamino group, dimethylamino group, methanesulfonylamino group, acetyl group, propionyl group, methoxycarbonyl group, benzoyl group, $C_{1-3}$alkyl group, $C_{1-3}$alkoxy group, 3- to 7-membered heterocyclic group.

"Purification" refers to any act that enhances the purity of a substance of interest and reduces the concentration of substances other than the substance of interest below the concentration prior to the purification. Various methods such as precipitation, recrystallization, sublimation, distillation, solvent extraction, use of molecular sieve, and application of various chromatographies can be used for purification. Purification does not include filtration using a filter paper or Celite.

In the compounds of the present invention represented by formula (I), the preferred Y, $P^1$, $P^2$, $P^3$, $P^4$, $R^1$, $R^2$, $R^3$, $R^4$, and $R^5$ are the following, but the technical scope of the present invention is not limited to the scope of compounds disclosed below.

Y is preferably a group represented by formula (Ya), (Yb), or (Yc), more preferably a group represented by formula (Ya) or (Yb), and most preferably a group represented by formula (Ya).

Examples of $P^1$ and $P^2$ include those that are identical or different, and each independently
(1) a hydrogen atom,
(2) a $C_{1-6}$alkyl group (the alkyl group is optionally substituted with one to three groups independently selected from the group consisting of a phenyl group, a halogen atom, a hydroxyl group, and a $C_{1-6}$alkoxy group),
(3) a silyl group (the silyl group is substituted with three substituents independently selected from the group consisting of a $C_{1-6}$alkyl group and a phenyl group),
(4) a phenyl group (the phenyl group is optionally substituted with one to three groups independently selected from the group consisting of a halogen atom, a hydroxyl group, a nitro group, a $C_{1-6}$alkyl group, and a $C_{1-6}$alkoxy group),
(5) a $C_{1-6}$alkylcarbonyl group (the alkyl is optionally substituted with one to three groups independently selected from the group consisting of a halogen atom, a hydroxyl group, and a $C_{1-6}$alkoxy group),
(6) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group), or
(7) a $C_{3-7}$cycloalkyl group (the cycloalkyl group is optionally substituted with one to three groups independently selected from the group consisting of a halogen atom, a hydroxyl group, and a $C_{1-6}$alkoxy group); and
   wherein when $P^1$ and $P^2$ are identical or different, and each independently a $C_{1-6}$alkyl group, a phenyl group, a $C_{1-6}$alkylcarbonyl group, or a $C_{3-7}$cycloalkyl group, they may be taken together to form a cyclic ketal that is optionally substituted with 1 to 4 groups independently selected from the group consisting of a $C_{1-6}$alkyl group, a halogen atom, a hydroxyl group, a nitro group, and a $C_{1-6}$alkyl group,
   wherein $P^1$ and $P^2$ are not both hydrogen atoms.

Examples of $P^1$ and $P^2$ include those that are identical or different, and each independently
(1) a hydrogen atom,
(2) a $C_{1-6}$alkyl group optionally substituted with one to three groups independently selected from the group consisting of a halogen atom and a $C_{1-6}$alkoxy group,
(3) a silyl group optionally substituted with one to three $C_{1-6}$alkyl groups,
(4) a phenyl group,
(5) a benzyl group, or
(6) a $C_{1-6}$alkylcarbonyl group; and
$P^1$ and $P^2$ that are taken together to form a cyclic ketal selected from the group consisting of
(7) 1,3-dioxolane optionally substituted with one to four groups independently selected from the group consisting of a $C_{1-6}$alkyl group, a $C_{1-6}$alkoxy group, a hydroxyl group, and a phenyl group,
(8) 1,3-dioxolane-4-one,
(9) 1,3-dioxolane-4,5-dione,
(10) 1,3-dioxane optionally substituted with one to four groups independently selected from the group consisting of a $C_{1-6}$alkyl group, a $C_{1-6}$alkoxy group, a hydroxyl group, and a phenyl group,
(11) 1,3-dioxane-4-one,
(12) 1,3-dioxane-4,6-dione, and
(13) benzo[d][1,3]dioxole.

More preferred examples of $P^1$ and $P^2$ include those that are identical or different, and each independently a $C_{1-6}$alkyl group or a $C_{1-6}$alkylcarbonyl group, and $P^1$ and $P^2$ that are taken together to form a cyclic ketal selected from the group consisting of 1,3-dioxolane optionally substituted with one to four $C_{1-6}$alkyl groups and 1,3-dioxane optionally substituted with one to four $C_{1-6}$alkyl groups.

Still more preferred examples of $P^1$ and $P^2$ include those that are identical or different, and each independently a methyl group, an ethyl group, a propyl group, an isopropyl group, a butyl group, a tert-butyl group, a pentyl group, or an acetyl group, and $P^1$ and $P^2$ that are taken together to form a cyclic ketal selected from the group consisting of 1,3-dioxolane, 4-methyl-1,3-dioxolane, 4,5-dimethyl-1,3-dioxolane, 4,4,5,5-tetramethyl-1,3-dioxolane, 1,3-dioxane, 4-methyl-1,3-dioxane, 5-methyl-1,3-dioxane, and 5,5-dimethyl-1,3-dioxane.

The most preferred examples of $P^1$ and $P^2$ include those that are taken together to form 1,3-dioxolane or 1,3-dioxane.

In yet another embodiment, the most preferred examples of $P^1$ and $P^2$ include those that are taken together to form 1,3-dioxane.

In yet another embodiment, preferred examples of $P^1$ and $P^2$ include those that are identical or different, and each independently a methyl group, an ethyl group, a propyl group, an isopropyl group, a butyl group, a tert-butyl group, a pentyl group, a 2-methoxy-2-butyl group, a chloroethyl group, a trichloroethyl group, a trimethylsilyl group, a triethylsilyl group, a tert-butyldimethylsilyl group, a benzyl group, and an acetyl group, or $P^1$ and $P^2$ that are taken together to form a cyclic ketal selected from the group consisting of 1,3-dioxolane, 4-methyl-1,3-dioxolane, 4,5-dimethyl-1,3-dioxolane, 4,4,5,5-tetramethyl-1,3-dioxolane, 1,3-dioxolane-4-one, 1,3-dioxolane-4,5-dione, 1,3-dioxane, 4-methyl-1,3-dioxane, 5-methyl-1,3-dioxane, 5,5-dimethyl-1,3-dioxane, 1,3-dioxane-4-one, and 1,3-dioxane-4,6-dione.

Examples of $P^3$ include
(1) a $C_{1-6}$alkyl group (the alkyl group is optionally substituted with one to three groups independently selected from the group consisting of
   (a) a halogen atom,
   (b) a $C_{1-6}$alkoxy group,
   (c) a silyloxy group substituted with three groups independently selected from the group consisting of a $C_{1-6}$alkyl group and a phenyl group,
   (d) a silyl group substituted with three groups independently selected from the group consisting of a $C_{1-6}$alkyl group and a phenyl group, and
   (e) a phenyl group optionally substituted with one to three groups independently selected from the group consisting of a halogen atom, a methoxy group, and a nitro group);
(2) a silyl group substituted with three substituents independently selected from the group consisting of a $C_{1-6}$alkyl group and a phenyl group;

(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^3$ in the formula (Yb) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{1-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups);
(14) a formyl group; and
(15) a hydrogen atom.

Preferred examples of $P^3$ include
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group.
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group,
(10) an allyloxycarbonyl group, and
(11) a hydrogen atom.

More preferred examples of $P^3$ include
(1) a $C_{1-6}$alkyl group optionally substituted with one to three $C_{1-6}$alkoxy groups,
(2) a silyl group substituted with three substituents independently selected from the group consisting of a $C_{1-6}$alkyl group and a phenyl group, and
(3) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^3$ in the formula (Yb) is attached).

Still more preferred examples of $P^3$ include a methoxymethyl group, a tert-butyl group, a 1-ethoxyethyl group, a 2-tetrahydropyranyl group, a 2-tetrahydrofuranyl group, a trimethylsilyl group, a triethylsilyl group, and a tert-butyldimethylsilyl group.

The most preferred examples of $P^3$ include a 2-tetrahydropyranyl group, a trimethylsilyl group, and a tert-butyldimethylsilyl group.

As another embodiment, preferred examples of $P^3$ include a methoxymethyl group, a tert-butyl group, a 1-ethoxyethyl group, a 2-tetrahydropyranyl group, a 2-tetrahydrofuranyl group, an allyl group, a benzyl group, a trimethylsilyl group, a triethylsilyl group, a tert-butyl dimethylsilyl group, a formyl group, an acetyl group, a propionyl group, a trifluoroacetyl group, a benzyloxycarbonyl group, an allyloxycarbonyl group, and a tert-butyloxycarbonyl group.

Examples of $P^4$ include
(1) a $C_{1-6}$alkyl group (the alkyl group is optionally substituted with one to three groups independently selected from the group consisting of
  (a) a halogen atom,
  (b) a $C_{1-6}$alkoxy group,
  (c) a silyloxy group substituted with three groups independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group);
(2) a silyl group substituted with three substituents independently selected from the group consisting of a $C_{1-6}$alkyl group and a phenyl group;
(3) a 3- to 8-membered monocyclic heterocyclic group (wherein the heterocyclic group has at least one or more oxygen atoms in the ring and a carbon atom adjacent to the oxygen atom(s) is bound to the oxygen atom to which $P^4$ in the formula (Yc) is attached);
(4) a $C_{2-6}$alkenyl group;
(5) a phenyl group (the phenyl group is optionally substituted with one to three groups independently selected from the group consisting of a halogen atom, a nitro group, and a $C_{1-6}$alkoxy group);
(6) a $C_{1-6}$alkylcarbonyl group (the alkyl is optionally substituted with one to three groups independently selected from the group consisting of a halogen atom, a hydroxyl group, a phenoxy group, a phenyl group, and a $C_{1-6}$alkoxy group);
(7) a phenylcarbonyl group (the phenyl is optionally substituted with one to three groups independently selected from the group consisting of a halogen atom, a hydroxyl group, a nitro group, a $C_{2-6}$alkyl group, and a $C_{1-6}$alkoxy group);
(8) a $C_{1-6}$alkyloxycarbonyl group (the alkyl is optionally substituted with one to three groups independently selected from the group consisting of a halogen atom, a hydroxyl group, a $C_{1-6}$alkoxy group, and a phenyl group);
(9) a phenyloxycarbonyl group (the phenyl is optionally substituted with one to three groups independently selected from the group consisting of a halogen atom, a hydroxyl group, a nitro group, a $C_{1-6}$alkyl group, and a $C_{1-6}$alkoxy group);
(10) a $C_{2-6}$alkenyloxycarbonyl group;
(11) an aminocarbonyl group (the amino is optionally substituted with one to two groups independently selected from the group consisting of a $C_{1-6}$alkyl group and a phenyl group);
(12) a $C_{1-6}$alkylsulfonyl group;
(13) a phenylsulfonyl group (the phenyl is optionally substituted with one to three $C_{1-6}$alkyl groups); and
(14) a formyl group.

Preferred examples of $P^4$ include
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which $P^4$ in the formula (Yc) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group, and
(10) an allyloxycarbonyl group.

More preferred examples of $P^4$ include
(1) a $C_{1-6}$alkyl group optionally substituted with one to three $C_{1-6}$alkoxy groups;
(2) a silyl group substituted with three substituents independently selected from the group consisting of a $C_{1-6}$alkyl group and a phenyl group; and
(3) a 5- or 6-membered monocyclic saturated heterocyclic group (wherein the saturated heterocyclic group has at least one or more oxygen atoms in the ring and a carbon atom adjacent to the oxygen atom(s) is bound to the oxygen atom to which $P^4$ in the formula (Yc) is attached).

Still more preferred examples of $P^4$ include a methoxymethyl group, a tert-butyl group, a 1-ethoxyethyl group, a 2-tetrahydropyranyl group, a 2-tetrahydrofuranyl group, a trimethylsilyl group, a triethylsilyl group, and a tert-butyldimethylsilyl group The most preferred examples of $P^4$ include a 2-tetrahydropyranyl group, a trimethylsilyl group, and a tert-butyldimethylsilyl group.

As another embodiment, preferred examples of $P^4$ include a methoxymethyl group, a tert-butyl group, a 1-ethoxyethyl group, a 2-tetrahydropyranyl group, a 2-tetrahydrofuranyl group, an allyl group, a benzyl group, a trimethylsilyl group, a triethylsilyl group, a tert-butyl dimethylsilyl group, a formyl group, an acetyl group, a propionyl group, a trifluoroacetyl group, a benzyloxycarbonyl group, an allyloxycarbonyl group, and a tert-butyloxycarbonyl group.

Preferred examples of $R^1$ include a $C_{1-10}$alkyl group optionally substituted with one to three groups independently selected from the group consisting of a halogen atom, a hydroxyl group, a $C_{1-6}$alkoxy group, a $C_{3-10}$ cycloalkyl group, a $C_{6-10}$aryl group, and a 3- to 12-membered monocyclic or polycyclic heterocyclic group.

More preferred examples of $R^1$ include a $C_{1-10}$alkyl group optionally substituted with one to three groups independently selected from the group consisting of a halogen atom, a $C_{1-6}$alkoxy group, and a $C_{3-10}$cycloalkyl group.

$R^1$ is still more preferably a $C_{1-6}$alkyl group.

$R^1$ is the most preferably a methyl group.

Preferred examples of $R^2$ include a $C_{1-10}$alkyl group optionally substituted with one to three groups independently selected from the group consisting of a halogen atom, a hydroxyl group, a $C_{1-6}$alkoxy group, a $C_{3-10}$ cycloalkyl group, a $C_{6-10}$aryl group, and a 3- to 12-membered monocyclic or polycyclic heterocyclic group.

More preferred examples of $R^2$ include a $C_{1-10}$alkyl group optionally substituted with one to three groups independently selected from the group consisting of a halogen atom, a $C_{1-6}$alkoxy group, and a $C_{3-10}$cycloalkyl group.

$R^2$ is still more preferably a $C_{1-6}$alkyl group.

$R^2$ is the most preferably a methyl group.

Preferred examples of $R^3$ include a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

More preferred examples of $R^3$ include a $C_{1-10}$alkyl group optionally substituted with one to three groups independently selected from the group consisting of a halogen atom, a $C_{1-6}$alkoxy group, and a $C_{3-10}$cycloalkyl group.

$R^3$ is still more preferably a $C_{1-6}$alkyl group.

$R^3$ is the most preferably methyl group.

Preferred examples of $R^4$ and $R^5$ are those that are identical or different, and each independently
(1) a hydrogen atom, or
(2) a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

More preferred examples of $R^4$ and $R^5$ are those that are identical or different, and each independently
(1) a hydrogen atom, or
(2) a $C_{1-10}$alkyl group optionally substituted with one to three groups independently selected from the group consisting of a halogen atom, a $C_{1-6}$alkoxy group, and a $C_{3-10}$cycloalkyl group.

Still more preferred examples of $R^4$ and $R^5$ include those that are identical or different, and each independently
(1) a hydrogen atom, or
(2) a $C_{1-6}$alkyl group.

The most preferred examples of $R^4$ and $R^5$ include a hydrogen atom.

Preferred compounds represented by formula (I) include the following compounds. Therefore, it is understood that tautomers, stereoisomers, mixtures or racemates, optionally pharmaceutically acceptable salts, and solvate of the following preferred compounds are also preferred in a preferred embodiment.

Preferred embodiments of the compounds represented by formula (I) include the following (A).
(A)
A compound, or a tautomer thereof, or an optionally pharmaceutically acceptable salt thereof, wherein Y is a group represented by (Ya), (Yb), or (Yc)
wherein $P^1$ and $P^2$ are identical or different, and each independently
(1) a hydrogen atom,
(2) a $C_{1-6}$alkyl group optionally substituted with one to three groups independently selected from the group consisting of a halogen atom and a $C_{1-6}$alkoxy group,
(3) a silyl group optionally substituted with one to three $C_{1-6}$alkyl groups,
(4) a phenyl group,
(5) a benzyl group, or
(6) a $C_{1-6}$alkylcarbonyl group; or
$P^1$ and $P^2$ are taken together to form a cyclic ketal selected from the group consisting of
(7) 1,3-dioxolane optionally substituted with one to four groups independently selected from the group consisting of a $C_{1-6}$alkyl group, a $C_{1-6}$alkoxy group, a hydroxyl group, and a phenyl group,
(8) 1,3-dioxolane-4-one,
(9) 1,3-dioxolane-4,5-dione,
(10) 1,3-dioxane optionally substituted with one to four groups independently selected from the group consisting of a $C_{1-6}$alkyl group, a $C_{1-6}$alkoxy group, a hydroxyl group, and a phenyl group,
(11) 1,3-dioxane-4-one,
(12) 1,3-dioxane-4,6-dione, and
(13) benzo[d][1,3]dioxole wherein P³ is
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which P³ in the formula (Yb) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group,
(10) an allyloxycarbonyl group, or
(11) a hydrogen atom,
wherein P⁴ is
(1) a $C_{1-6}$alkyl group (the alkyl group is optionally substituted with one to three groups independently selected from the group consisting of a halogen atom, a $C_{1-6}$alkoxy group, a trimethylsilyloxy group, and a trimethylsilyl group),
(2) a benzyl group,
(3) a trityl group,
(4) a silyl group substituted with three substituents independently selected from the group consisting of a $C_{1-6}$alkyl group and a phenyl group,
(5) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which P⁴ in the formula (Yc) is attached),
(6) a $C_{2-6}$alkenyl group,
(7) a $C_{1-6}$alkylcarbonyl group (the alkyl is optionally substituted with one to three fluorine atoms),
(8) a $C_{1-6}$alkyloxycarbonyl group,
(9) a benzyloxycarbonyl group, or
(10) an allyloxycarbonyl group,
wherein R² is a $C_{1-10}$alkyl group optionally substituted with one to three groups independently selected from the group consisting of a halogen atom, a $C_{1-6}$alkoxy group, and a $C_{3-10}$cycloalkyl group,
wherein R³ is a $C_{1-10}$alkyl group optionally substituted with one to three groups independently selected from the group consisting of a halogen atom, a $C_{1-6}$alkoxy group, and a $C_{3-10}$cycloalkyl group,
wherein R⁴ and R⁵ are identical or different, and each independently
(1) a hydrogen atom, or
(2) a $C_{1-10}$alkyl group optionally substituted with one to three groups independently selected from the group consisting of a halogen atom, a $C_{1-6}$alkoxy group, and a $C_{3-10}$cycloalkyl group.

A more preferred embodiment of the compounds represented by formula (I) include the following (B).
(B)
A compound, or a tautomer thereof, or an optionally pharmaceutically acceptable salt thereof, wherein Y is a group represented by (Ya) or (Yb),
wherein P¹ and P² are more preferably identical or different, and each independently a $C_{1-6}$alkyl group or a $C_{1-6}$alkylcarbonyl group, or
P¹ and P² are taken together to form a cyclic ketal selected from the group consisting of 1,3-dioxolane optionally substituted with one to four $C_{1-6}$alkyl groups or 1,3-dioxane optionally substituted with one to four $C_{1-6}$alkyl groups,
wherein P₃ is
(1) a $C_{1-6}$alkyl group optionally substituted with one to three $C_{1-6}$alkoxy groups,
(2) a silyl group substituted with three substituents independently selected from the group consisting of a $C_{1-6}$alkyl group and a phenyl group, or
(3) a 5- or 6-membered monocyclic saturated heterocyclic group (wherein the heterocyclic group has at least one or more oxygen atoms in the ring and a carbon atom adjacent to the oxygen atom(s) is bound to the oxygen atom to which P³ in the formula (Yb) is attached),
wherein R² is a $C_{1-6}$alkyl group, and
wherein R³ is a $C_{1-6}$alkyl group.

A still more preferred embodiment of the compounds represented by formula (I) include the following (C).
(C)
A compound, or a tautomer thereof, or an optionally pharmaceutically acceptable salt thereof,
wherein Y is a group represented by (Ya) or (Yb),
wherein P¹ and P² are each independently a methyl group, an ethyl group, a propyl group, an isopropyl group, a butyl group, a tert-butyl group, a pentyl group, or an acetyl group, or P¹ and P² are taken together to form a cyclic ketal selected from the group consisting of 4-methyl-1,3-dioxolane, 4,5-dimethyl-1,3-dioxolane, 4,4,5,5-tetramethyl-1,3-dioxolane, 1,3-dioxane, 4-methyl-1,3-dioxane, 5-methyl-1,3-dioxane, and 5,5-dimethyl-1,3-dioxane,
wherein P³ is a methoxymethyl group, a tert-butyl group, a 1-ethoxyethyl group, a 2-tetrahydropyranyl group, a 2-tetrahydrofuranyl group, a trimethylsilyl group, a triethylsilyl group, or a tert-butyldimethylsilyl group,
wherein R² is a $C_{1-6}$alkyl group, and
wherein R³ is a $C_{1-6}$alkyl group.

A still more preferred embodiment of the compounds represented by formula (I) include the following (D).
(D)
A compound, or a tautomer thereof, or an optionally pharmaceutically acceptable salt thereof,
wherein Y is a group represented by (Ya) or (Yb),
wherein P¹ and P² are taken together to form 1,3-dioxane,
wherein P³ is a 2-tetrahydropyranyl group, a trimethylsilyl group, or a tert-butyldimethylsilyl group,
wherein R² is a methyl group, and
wherein R³ is a methyl group.

While the present invention is explained in more detail hereinafter with preferred embodiments, the technical scope of the present invention is not limited by the preferred embodiments. The present invention may also be altered to the extent that the altered invention remains within the scope of the present invention. It should be noted that compound names in the following preferred embodiments do not always follow the IUPAC nomenclature.

The following abbreviations may be used to simplify the descriptions herein. DMF: N,N-dimethylformamide, Me: methyl group, TMS: trimethylsilyl group.

The production method of a compound of formula (I) in the present invention, or a tautomer thereof, a stereoisomer thereof, a mixture or racemate thereof, or an optionally pharmaceutically acceptable salt thereof or solvate thereof (which are used as a production intermediate of 2-alkylcarbonylnaphtho[2,3-b]furan-4,9-dione) is discussed below. Intermediates of 2-alkylcarbonylnaphtho[2,3-b]furan-4,9-dione and 2-alkylcarbonylnaphtho[2,3-b]furan-4,9-dione can be produced from a known compound by the following production method and a method corresponding thereto or appropriately combining synthesis methods that are well known to those skilled in the art.

While a compound obtained in each step can be used in the next reaction directly as a reaction solution or as a compound, the compound can also be isolated from a reaction mixture by a conventional method, and readily purified by separation means such as recrystallization, distillation, or chromatography.

Unless specifically noted otherwise, each symbol of compounds in the following reactions is synonymous with the systems discussed above.

Production Method

[Chemical formula 19]

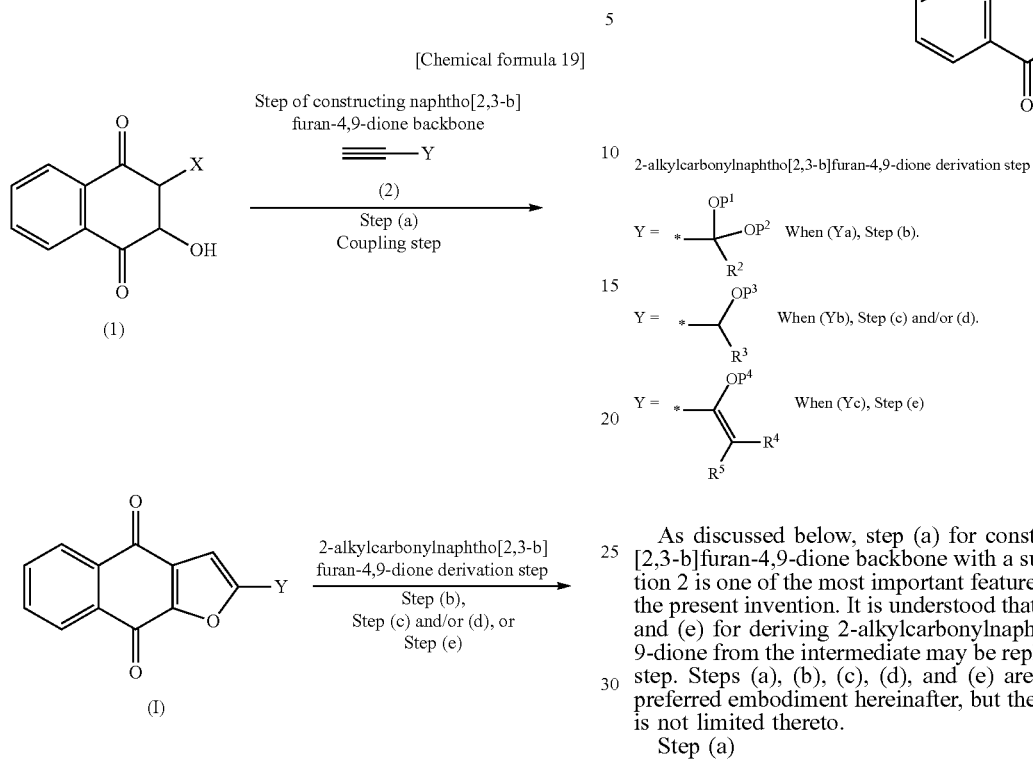
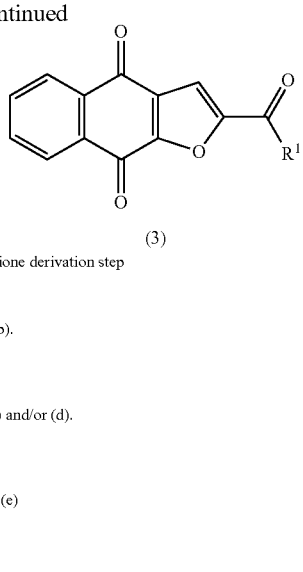

As discussed below, step (a) for constructing a naphtho[2,3-b]furan-4,9-dione backbone with a substitution at position 2 is one of the most important features in the method of the present invention. It is understood that steps (b), (c), (d), and (e) for deriving 2-alkylcarbonylnaphtho[2,3-b]furan-4,9-dione from the intermediate may be replaced with another step. Steps (a), (b), (c), (d), and (e) are explained with a preferred embodiment hereinafter, but the present invention is not limited thereto.

Step (a)

[Chemical formula 20]

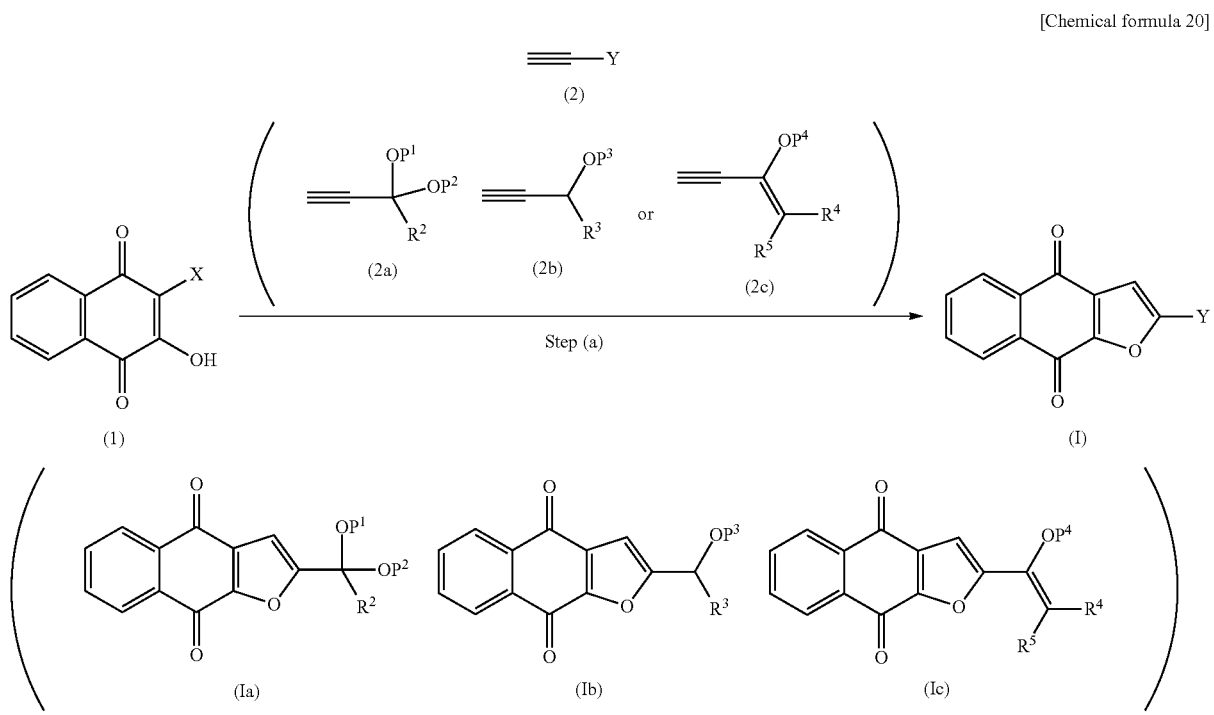

wherein X, Y, $P^1$, $P^2$, $P^3$, $P^4$, $R^2$, $R^3$, $R^4$, and $R^5$ are as defined in item 1 and/or other items.

For the compounds represented by formula (1), commercially available compounds can be used or the compounds can be produced by a method described in various documents. For instance, a compound in which X is a phenyliodonio group, a chlorine atom, a bromine atom, or an iodine atom can be produced with the method described by Hatzigrigoriou et al. in Liebigs Annalen der Chemie, (2), 167-70; 1989. A compound in which X is a bromine atom can be produced by the method described in Tetrahedron Letters 53 (2012) 191-195. A compound in which X is an iodine atom can be produced by the method described in Tetrahedron Letters 52 (2011) 6554-6559.

For compounds represented by formula (2a) where Y is formula (Ya) in formula (2), a commercially available compound can be used, or the compounds can be produced by the method described in documents such as Wuts, P. G. M.; Greene, T. W. Protective Groups in Organic Synthesis, 5th ed., WILEY, 2014. When a protecting group for a carbonyl group is for example 1,3-dioxolane, such a compound can be produced by a condensation reaction between 3-butyne-2-one and ethylene glycol in a suitable solvent in the presence of an acidic catalyst.

For compounds represented by formula (2b) where Y is formula (Yb) in formula (2), a commercially available compound can be used, or the compounds can be produced by the method described in documents such as Wuts, P. G. M.; Greene, T. W. Protective Groups in Organic Synthesis, 5th ed., WILEY, 2014. When a protecting group for a hydroxyl group is for example an acetyl group, such a compound can be produced by a condensation reaction between 3-butyne-2-ol and acetyl chloride in a suitable solvent in the presence of a base. Further, when a protecting group for alcohol is for example a trimethylsilyl group, such a compound can be produced by reacting chlorotrimethylsilane with 3-butyne-2-ol in a suitable solvent in the presence of a base.

For compounds represented by formula (2c) where Y is formula (Yc) in formula (2), a commercially available compound can be used, or the compounds can be produced by the method described in documents such as Wuts, P. G. M.; Greene, T. W. Protective Groups in Organic Synthesis, 5th ed., WILEY, 2014. When a protecting group for an enol group is for example an acetyl group, such a compound can be produced by a condensation reaction between 3-butyne-2-one and acetyl chloride in a suitable solvent in the presence of a base. Further, when $P^4$ is a triethylsilyl group, such a compound can be produced by reacting triethylsilyl trifluoromethanesulfonate with 3-butyne-2-one in a suitable solvent in the presence of a base.

This step is a step for obtaining a compound represented by formula (I) (formula (Ia), (Ib), or (Ic)) by reacting a compound represented by formula (2) (formula (2a), (2b), or (2c)) with a compound represented by formula (1) in a solvent in the presence of a base and a metal or a metal compound. Examples of bases used in this step include inorganic bases such as potassium carbonate and cesium carbonate and organic bases such as pyridine, N,N,N',N'-tetramethylethane-1,2-diamine, 1,4-diazabicyclo[2.2.2]octane, and triethylamine. Examples of the metal or metal compound used in this step include metal copper and copper compounds. The metal copper and copper compound is preferably metal copper (0), copper(I) oxide, copper(I) acetate, copper(I) bromide, or copper(II) oxide, more preferably metal copper (0) or copper(I) oxide, and most preferably copper(I) oxide. This reaction surprisingly does not require addition of a metal palladium or palladium compound that is required in a normal coupling reaction when metal copper or a copper compound is used as the metal or a metal compound.

The solvent used in this step is not particularly limited as long as the boiling point is at or above the reaction temperature of this reaction, but examples thereof include ethylene glycol, N,N-dimethylacetamide, N,N-dimethylformamide, dimethylsulfoxide, N-methyl-2-pyrrolidone, monochlorobenzene, and toluene. If a basic solvent is used as the solvent, there is no need for an addition base. Examples of basic solvents include amine-based solvents such as N-methylpiperidine, N,N,N',N'-tetramethylethane-1,2-diamine, N,N-diisopropylethylamine, N,N-dimethylaniline, pyridine, 2-picoline, 3-picoline, 4-picoline, and 2,4-dimethylpyridine. The basic solvent is preferably pyridine, 4-picoline, or N-methylpiperidine, and more preferably pyridine.

With respect to 1 equivalent of the compound represented by formula (1), the amount of compound represented by formula (2) used is generally 0.8 equivalents to 10 equivalents, preferably 0.9 equivalents to 5 equivalents, more preferably 1.0 equivalent to 2 equivalent, and most preferably 1.0 equivalent to 1.5 equivalents.

With respect to 1 equivalent of the compound represented by formula (1), the amount of metal or a metal compound used is generally 0.05 equivalents to 5 equivalents, preferably 0.8 equivalents to 3 equivalents and more preferably 1.0 equivalent to 2.0 equivalents.

The reaction time is generally about 1 to 12 hours, preferably 2 to 8 hours, and more preferably 3 to 6 hours.

The reaction temperature is generally 20° C. to 200° C., preferably 70° C. to 150° C., and more preferably 80 to 120° C. Preferred $P^1$, $P^2$, $P^3$, $P^4$, and $P^5$ have been discussed above.

Step (b)

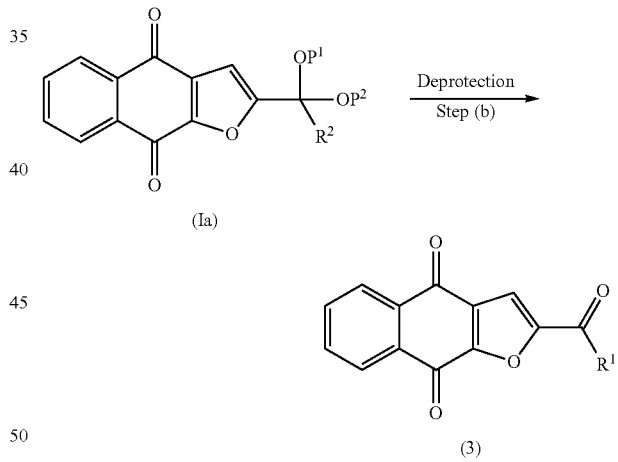

[Chemical formula 21]

wherein $P^1$, $P^2$, $R^1$, and $R^2$ are as defined in item 1, and $R^1$ and $R^2$ are define the same.

This step is a step for obtaining 2-alkylcarbonylnaphtho[2,3-b]furan-4,9-dione represented by formula (3) by deprotecting $P^1$ and $P^2$ which are protecting groups for a carbonyl group of the compound represented by formula (Ia) obtained using formula (2a) in production step (a) in a solvent in the presence of an acid, base, or various deprotection reagents. This step is performed by first isolating the compound represented by formula (Ia). This step can also perform steps (a) and (b) in one-pot synthesis, or perform steps (a) and (b) by connecting the steps by telescoping.

When first isolating the compound, a method can comprise a step of purifying a product of step (a). In this case, the solvent used in step (b) can be water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, or a mixture solvent thereof.

When steps (a) and (b) are performed in one-pot synthesis or steps (a) and (b) are performed by connecting the steps by telescoping, step (b) is performed without purifying the product of step (a). In such a case, the solvent used in step (b) can be a solvent that can be exchanged with a solvent used in step (a). The solvent used in step (a) can be pyridine, and the solvent used in step (b) can be water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, or a mixture solvent thereof.

Examples of acids used in this step include hydrochloric acid, hydrobromic acid, trifluoroacetic acid, sulfuric acid, p-toluenesulfonic acid, formic acid, and acetic acid. Examples of bases used in this step include lithium hydroxide, sodium hydroxide, potassium hydroxide, lithium carbonate, sodium carbonate, potassium carbonate, and cesium carbonate. Examples of deprotection reagents used in this step include silica gel, dimethylbromoborane, trimethylsilyl iodide, lithium tetrafluoroborate, and aluminum iodide. Examples of solvents used in this step include water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, and a mixture solvent thereof.

The reaction time is generally about 1 to 12 hours and preferably 2 to 6 hours.

The amount of acid, base, or deprotection reagent used is generally 0.1 to 20 equivalents of the amount of compound of formula (Ia) used, preferably 0.1 to 10 equivalents, and more preferably 1.0 to 10 equivalents. The reaction temperature is generally −78° C. to 100° C. and preferably 20° C. to 90° C.

Step (c) and Step (d)

[Chemical formula 22]

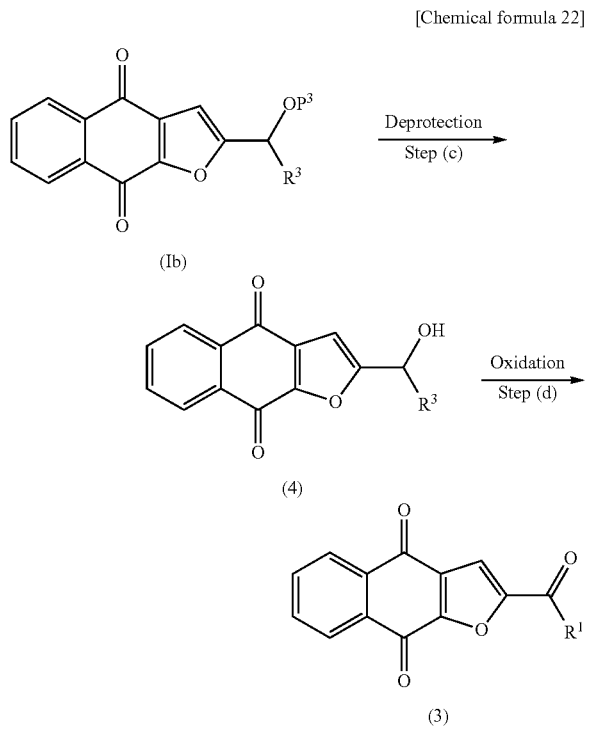

wherein $P^3$ and $R^3$ are as defined in item 1, and $R^1$ and $R^3$ are defined the same.

Step (c)

This step is a step for obtaining a compound of formula (4) by deprotecting $P^3$ which is a protecting group for a hydroxyl group of the compound represented by formula (Ib) obtained using formula (2b) in production step (a) in a suitable solvent in the presence of an acid, base, or various deprotection reagents. When $P^3$ is a hydrogen atom, this step can be omitted. This step is performed by first isolating the compound represented by formula (Ib). This step can also perform steps (a) and (c) in one-pot synthesis, or perform steps (a) and (c) by connecting the steps by telescoping. Examples of acids used in this step include hydrochloric acid, hydrobromic acid, trifluoroacetic acid, sulfuric acid, p-toluenesulfonic acid, formic acid, and acetic acid. Examples of bases used in this step include lithium hydroxide, sodium hydroxide, potassium hydroxide, lithium carbonate, sodium carbonate, potassium carbonate, and cesium carbonate. Examples of deprotection reagents used in this step include silica gel, dimethylbromoborane, trimethylsilyl iodide, lithium tetrafluoroborate, aluminum iodide, and the like.

Examples of solvents used in this step include water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, and a mixture solvent thereof.

The amount of acid, base, or deprotection reagent used is generally 0.1 to 20 equivalents of the amount of compound of formula (Ib) used, preferably 0.1 to 10 equivalents, and more preferably 1.0 to 10 equivalents.

The reaction time is generally about 1 to 12 hours and preferably 2 to 6 hours.

The reaction temperature is generally −78° C. to 100° C. and preferably 20° C. to 90° C.

Step (d)

This step is a step for obtaining a compound of formula (3) by oxidizing a hydroxyl group of a compound of formula (4) obtained in production step (a) or production step (c) in a suitable solvent using an oxidant. This step is performed by first isolating the compound represented by formula (4). This step can also perform steps (a), (c) and (d) or steps (c) and (d) in one-pot synthesis, or perform steps (a), (c) and (d) or steps (c) and (d) by connecting the steps by telescoping.

The oxidation reaction can be performed in accordance with common conditions. Examples of oxidants used in this step include chromium oxide, chromic acid, pyridinium chlorochromate, sodium dichromate, pyridinium dichromate, manganese dioxide, sodium hypochlorite, sodium bromite, N-chlorosuccinimide, N-bromosuccinimide, dimethylsulfoxide and oxalyl chloride, 2,2,6,6-tetramethylpiperidinoxy, free radical (TEMPO), 2-azaadamantane-N-oxyl (AZADO), and 1-methyl-2-azaadamantane-N-oxyl (1-Me-AZADO). This step can use a co-oxidant as needed. Examples of co-oxidants include hypochlorite, bromite, N-chlorosuccinimide, and iodobenzene diacetate.

Examples of solvents used in this step include water, acetic acid, acetone, methylene chloride, chloroform, hexane, petroleum ether, pyridine, dimethylsufoxide, tetrahydrofuran, diethyl ether, acetic anhydride, N,N-dimethylacetamide, N,N-dimethylformamide, N-methyl-2-pyrrolidone, acetonitrile, and dioxane.

The amount of oxidant used, such as when pyridinium chlorochromate is used, is generally 1.5 to 2 equivalents to the amount of 2-(1-hydroxyethyl)naphtho[2,3-b]furan-4,9-dione used. The amount when dimethylsulfoxide or oxalyl chloride is used is generally 1.0 to 1.5 equivalents to the amount of 2-(1-hydroxyethyl)naphtho[2,3-b]furan-4,9-dione used. The amount when using 2,2,6,6-tetramethylpiperidinoxy, free radical (TEMPO), 2-azaadamantane-N-oxyl (AZADO), or 1-methyl-2-azaadamantane-N-oxyl (1-Me-AZADO) is generally 0.01 to 0.1 equivalents to the amount of 2-(1-hydroxyethyl)naphtho[2,3-b]furan-4,9-dione used. As a co-oxidant, 1.0 to 1.2 equivalents of hypochlorite, bromite, N-chlorosuccinimide, or iodobenzene diacetate is used.

The reaction time is generally 1 to 6 hours when for example pyridinium chlorochromate is used. When dimethylsulfoxide or oxalyl chloride is used, the time is generally 1 hour or less. When 2,2,6,6-tetramethylpiperidinoxy, free radical (TEMPO), 2-azaadamantane-N-oxyl (AZADO), or 1-methyl-2-azaadamantane-N-oxyl (1-Me-AZADO) is used, the time is generally 1 to 6 hours.

The reaction temperature is generally 0° C. to 30° C. when for example pyridinium chlorochromate is used. When dimethylsulfoxide or oxalyl chloride is used, the temperature is generally −78° C. When 2,2,6,6-tetramethylpiperidinoxy, free radical (TEMPO), 2-azaadamantane-N-oxyl (AZADO), or 1-methyl-2-azaadamantane-N-oxyl (1-Me-AZADO) is used, the temperature is generally 0° C. to 30° C.

Production Method (e)

[Chemical formula 23]

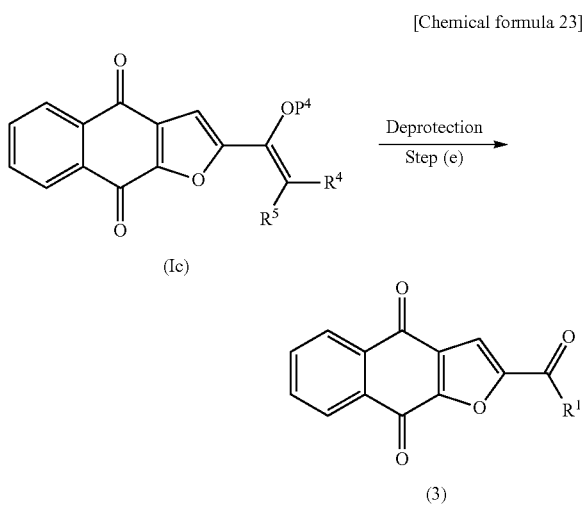

wherein $P^4$, $R^4$, and $R^5$ are as defined in item 1, and $—R^1$ is defined the same as $—CHR^4R^5$.

This step is a step for obtaining 2-alkylcarbonylnaphtho[2,3-b]furan-4,9-dione by deprotecting $P^4$ which is a protecting group of an enol group of the compound represented by formula (Ic) obtained using formula (2c) in production step (a) in a suitable solvent in the presence of an acid, base, or various deprotection reagents. This step is performed by first isolating the compound represented by formula (Ic). This step can also perform steps (a) and (e) in one-pot synthesis, or perform steps (a) and (e) by connecting the steps by telescoping.

Examples of acids used in this step include hydrochloric acid, hydrobromic acid, trifluoroacetic acid, sulfuric acid, p-toluenesulfonic acid, formic acid, and acetic acid. Examples of bases used in this step include lithium hydroxide, sodium hydroxide, potassium hydroxide, lithium carbonate, sodium carbonate, potassium carbonate, and cesium carbonate. Examples of deprotection reagents used in this step include silica gel, dimethylbromoborane, trimethylsilyl iodide, lithium tetrafluoroborate, aluminum iodide, and the like.

Examples of solvents used in this step include water, methanol, ethanol, acetone, diethyl ether, dichloromethane, chloroform, tetrahydrofuran, acetonitrile, dimethylsulfoxide, N,N-dimethylacetamide, N,N-dimethylformamide, N-methyl-2-pyrrolidone, pyridine, and a mixture solvent thereof.

The amount of acid, base, or deprotection reagent used is generally 0.1 to 20 equivalents of the amount of compound of formula (Ic) used, preferably 0.1 to 10 equivalents, and more preferably 1.0 to 10 equivalents.

The reaction time is generally about 1 to 12 hours and preferably 2 to 6 hours.

The reaction temperature is generally −78° C. to 100° C. and preferably 20° C. to 90° C.

A naphtho[2,3-b]furan-4,9-dione backbone with a substitution at position 2 can be produced at low cost, safely, with high purity, and at a high yield by the production method (a) of the present invention. Therefore, related substances that are useful as an intermediate of 2-alkylcarbonylnaphtho[2,3-b]furan-4,9-dione can be produced at a lower cost, safer, with a higher purity, and at a higher yield compared to conventional methods. Furthermore, 2-alkylcarbonylnaphtho[2,3-b]furan-4,9-dione that is useful as a pharmaceutical product can be produced at low cost, safely, with high purity, and at a high yield by subjecting the intermediate to steps (b), (c), and/or (d), or (e).

The compound of formula (1) in which X is a bromine atom is a low cost, safe, and stable compound. By using such a compound, using only copper(I) oxide as a metal compound, and performing step (a) in pyridine, a 2-alkylcarbonylnaphtho[2,3-b]furan-4,9-dione related substance (compound of formula (I)) can be produced at a high yield, with a high purity, at a low cost, safely, and readily. Surprisingly, a palladium catalyst that is generally essential in the coupling step is not required in the above reaction conditions. Palladium catalysts are expensive, and residual thereof in a pharmaceutical product would be problematic due to the toxicity thereof. Therefore, a coupling step that does not use a palladium catalyst is very useful in producing 2-alkylcarbonylnaphtho[2,3-b]furan-4,9-dione and related substances thereof from the viewpoint of price and safety.

With a compound of formula (Ia) or (Ic), 2-alkylcarbonylnaphtho[2,3-b]furan-4,9-dione of interest can be obtained in a form of a crystal at a high yield, with a high purity, at a low cost, safely, and readily by deprotecting protecting groups $P^1$ and $P^2$ or $P^4$ under normal reaction conditions.

With a compound of formula (Ib), a compound of formula (4) of interest can be obtained at a high yield, with a high purity, at a low cost, safely, and readily by deprotecting the protecting group $P^3$ under normal reaction conditions. With such a compound of formula (4), 2-alkylcarbonylnaphtho[2,3-b]furan-4,9-dione of interest can be obtained in a form of a crystal at a high yield, with a high purity, at a low cost, safely, and readily by oxidation in a suitable solvent.

The order of adding a reagent or the like is not limited to the order disclosed above.

The present invention is explained in further detail hereinafter with Reference Examples and Examples, but the present invention is not limited thereby. Compounds were identified with an elemental analysis value, a mass spectrum, a high performance liquid chromatography mass spectrometer (LCMS), infrared (IR) absorption spectra, Nuclear Magnetic Resonance (NMR) spectra, high performance liquid chromatography (HPLC), or the like.

The measurement conditions for high performance liquid chromatography (HPLC) are described below. The retention time is indicated by Rt (minutes). The measurement conditions used for measurement are described for each of the actual measurement values. In the following description, HPLC purity (area %) has been calculated by comparing each peak area using the following measurement conditions.

Column: phenomenex 1.7u C18 100A (50×2.1 mm)
Eluent: solution A: aqueous 0.05% trifluoroacetic acid solution, solution B: acetonitrile Gradient Condition

TABLE 1

| Minutes | A (%) | B (%) |
| --- | --- | --- |
| 0-1 | 90 | 10 |
| 1-6 | 90 → 6 | 10 → 94 |
| 6-11 | 6 | 94 |
| 11-11.1 | 6 → 90 | 94 → 10 |
| 11.1-20 | 90 | 10 |

Flow rate: 0.4 mL/min

Column temperature: 40° C.

Wavelength: 250 nm

Rt for each compound measured under the above measurement conditions is shown in the following Table.

TABLE 2

| Compound | Rt (minutes) |
| --- | --- |
| 2-bromo-3-hydroxynaphthalene-1,4-dione | 7.8 |
| 2-hydroxy-3-iodonaphthalene-1,4-dione | 9.3 |
| 3-phenyliodonio-1,2,4-trioxo-1,2,3,4-tetrahydronaphthalenide | 8.7 |
| 2-(2-methyl-1,3-dioxolane-2-yl)naphtho[2,3-b]furan-4,9-dione | 10.4 |
| 2-acetylnaphtho[2,3-b]furan-4,9-dione | 9.8 |
| 2-(2-methyl-1,3-dioxane-2-yl)naphtho[2,3-b]furan-4,9-dione | 10.5 |
| 2-(1-hydroxyethyl)naphtho[2,3-b]furan-4,9-dione | 9.4 |
| 2-(1-((tert-butyldimethylsilyl)oxy)ethyl)naphtho[2,3-b]furan-4,9-dione | 12.9 |
| 2-(1-((tetrahydro-2H-pyran-2-yl))oxy)ethyl)naphtho[2,3-b]furan-4,9-dione | 11.2 |

The following abbreviations may be used in the Reference Examples, Examples, and Tables in the Examples to simplify the descriptions herein.

Me: methyl

DMF: N,N-dimethylformamide

NMP: N-methyl-2-pyrrolidone

TMS: trimethylsilyl

TFA: trifluoroacetic acid

PCC: pyridinium chlorochromate

THF: tetrahydrofuran

DBU: 1,8-diazabicyclo[5.4.0]-7-undecene p-: parawt %: weight %

As symbols used in NMR, s indicates a single line, d indicates double lines, t indicates triple lines, q indicates quadruple lines, and m indicates multiple lines.

EXAMPLES

While the present invention is explained in more detail hereinafter with Examples and Reference Examples, the technical scope of the present invention is not limited by such Examples. The present invention may be altered to the extent that the altered invention remains within the scope of the present invention. It should be noted that compound names in the following Examples and Comparative Examples do not always follow the IUPAC nomenclature.

Reference Examples

Reference Example 1: Production of 2-bromo-3-hydroxynaphthalene-1,4-dione

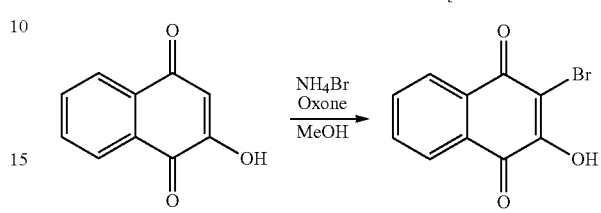

[Chemical formula 24]

Oxone® (55.62 g) was added little by little at 25° C., while stirring, into a methanol suspension (150 mL) of ammonium bromide (8.86 g) and 2-hydroxynaphthalane-1,4-dione (15.01 g). After 24 hours, a solid and a methanol solution were separated by filtration. The solid was washed with ethyl acetate and acetone. The organic layer was subjected to vacuum concentration to obtain 2-bromo-3-hydroxynaphthalene-1,4-dione (16.5 g, yield: 76%). Water and 5% sodium bisulfite solution were added to the methanol solution. The deposited crystal was filtered and subjected to vacuum drying to obtain 2-bromo-3-hydroxynaphthalene-1,4-dione (3.7 g, yield: 17%) (total yield of 93%).

$^1$H-NMR (400 MHz, CDCl$_3$) δ: 7.54-7.85 (m, 3H), 8.17 (dd, 1H, J=7.2 and 1.6 Hz), 8.24 (dd, 1H, J=7.6 and 1.6 Hz).

Reference Example 2: Production of 2-hydroxy-3-iodonaphthalene-1,4-dione

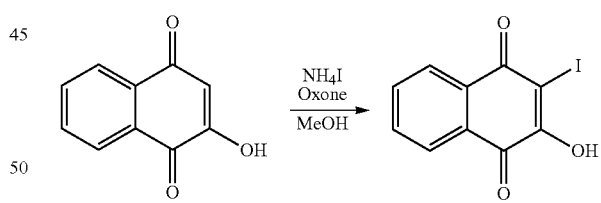

[Chemical formula 25]

Oxone® (37.1 g) was added little by little at 25° C., while stirring, into a methanol suspension (100 mL) of ammonium iodide (8.76 g) and 2-hydroxynaphthalane-1,4-dione (10.0 g). After 3.5 hours, a solid was filtered and washed with ethyl acetate. The organic layer was subjected to vacuum concentration. The residual was dissolved in ethyl acetate, and washed with water, aqueous 5% potassium iodide solution, and water in this order. After drying the organic layer with magnesium sulfate, the organic layer was subjected to vacuum concentration to obtain 16.8 g (98%) of black solid. The black solid was washed with isopropyl acetate and subjected to vacuum drying to obtain 2-hydroxy-3-iodonaphthalene-1,4-dione (11.8 g, yield: 68%).

$^1$H-NMR (400 MHz, CDCl$_3$) δ: 7.75-7.82 (m, 2H), 8.04 (s, 1H), 8.16-8.18 (m, 1H), 8.22-8.24 (m, 1H).

Reference Example 3: Production of 3-phenyliodonio-1,2,4-trioxo-1,2,3,4-tetrahydronaphthalenide

[Chemical formula 26]

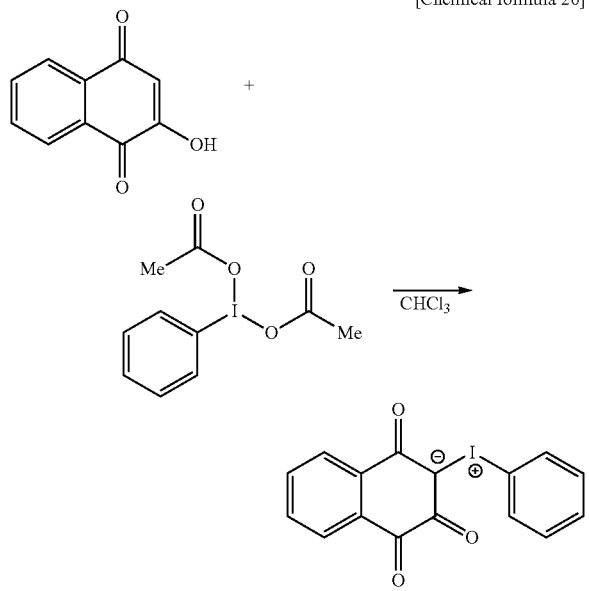

A chloroform (36.1 g) solution of iodobenzene diacetate (3.7 g) was dripped into a chloroform (50.5 g) solution of 2-hydroxynaphthalene-1,4-dione (2.0 g) at 0° C. while stirring. The mixture was stirred for 5 hours at room temperature. The deposited solid was filtered and then subjected to vacuum drying to obtain 3-phenyliodonio-1,2,4-trioxo-1,2,3,4-tetrahydronaphthalenide (3.9 g, yield: 89%)

$^1$H-NMR (400 MHz, DMSO-$d_6$) δ: 7.38-7.44 (m, 2H), 7.50-7.55 (m, 1H), 7.70-7.76 (m, 1H), 7.79-7.88 (m, 3H), 7.96-7.99 (m, 1H), 8.04-8.07 (m, 1H).

Reference Example 4: Production of 2-ethynyl-2-methyl-1,3-dioxolane

[Chemical formula 27]

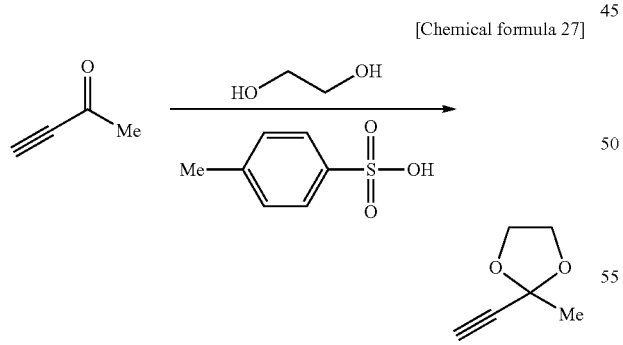

A dichloromethane (38 mL) solution of 3-butyne-2-one (5.2 g), ethylene glycol (4.7 g), and p-toluenesulfonic acid monohydrate (0.6 g) was heated and refluxed for 4 hours while removing the generated water with a trap. After cooling the reaction solution, sodium bicarbonate was added. The solution was filtered and subjected to vacuum concentration. The residual was distilled (50.0° C./50 hPa) to obtain 2-ethynyl-2-methyl-1,3-dioxolane (4.5 g, yield: 55%).

$^1$H-NMR (400 MHz, CDCl$_3$) δ: 1.68 (s, 3H), 2.45 (s, 1H), 3.94-4.10 (m, 4H).

Reference Example 5: Production of 2-ethynyl-2-methyl-1,3-dioxane

[Chemical formula 28]

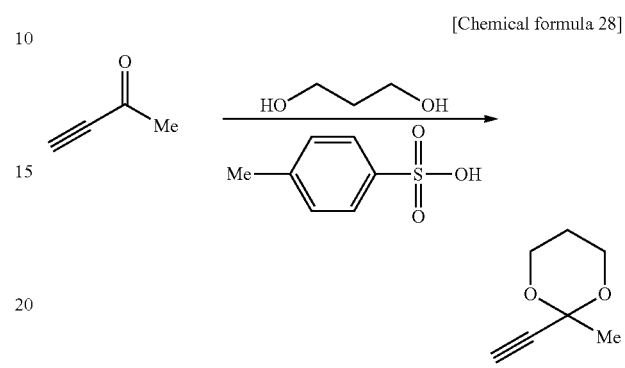

A dichloromethane (38 mL) solution of 3-butyne-2-one (5.0 g), propylene glycol (5.7 g), and p-toluenesulfonic acid monohydrate (0.6 g) was heated and refluxed for 3.5 hours while removing the generated water with a trap. After cooling the reaction solution, sodium bicarbonate was added. The solution was filtered and subjected to vacuum concentration. The residual was distilled (68.5° C./75 hPa) to obtain 2-ethynyl-2-methyl-1,3-dioxane (6.5 g, yield: 79%).

$^1$H-NMR (400 MHz, CDCl$_3$) δ: 1.30-1.35 (m, 1H), 1.59 (s, 3H), 1.98-2.03 (m, 1H), 2.60 (s, 1H), 3.84-3.89 (m, 2H), 4.17-4.24 (m, 2H).

EXAMPLES

While the present invention is explained in more detail hereinafter with Examples and Comparative Examples, the technical scope of the present invention is not limited by such Examples. The present invention may be altered to the extent that the altered invention remains within the scope of the present invention. It should be noted that compound names in the following Examples and Comparative Examples do not always follow the IUPAC nomenclature.

Example 1: Production method of 2-(2-methyl-1,3-dioxolane-2-yl)naphtho[2,3-b]furan-4,9-dione and 2-acetylnaphtho[2,3-b]furan-4,9-dione

[Chemical formula 29]

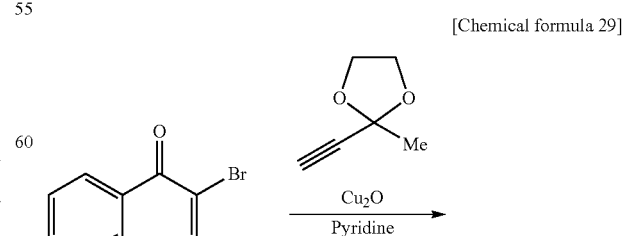

-continued

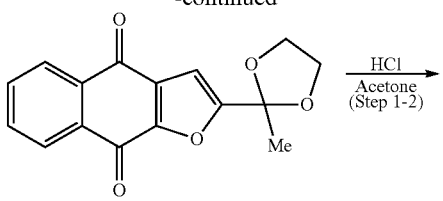

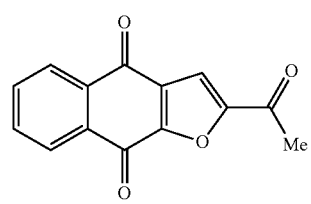

Step 1-1: Production of 2-(2-methyl-1,3-dioxolane-2-yl)naphtho[2,3-b]furan-4,9-dione 2-bromo-3-hydroxynaphthalene-1,4-dione (1.00 g) and copper(I) oxide (1.13 g; Aldrich) were placed in a flask. The gas was replaced with nitrogen. Pyridine (49.4 mL) and 2-ethynyl-2-methyl-1,3-dioxolane (0.49 g) were added. The reaction solution was stirred for 1 hour at 25° C., and then heated and refluxed for 4 hours. After cooling the reaction solution to room temperature, 3.5% hydrochloric acid (200 mL) and ethyl acetate (200 mL) were added, and the organic layer was separated. The organic layer was washed with 3.5% hydrochloric acid (200 mL), dried with magnesium sulfate, and then subjected to vacuum concentration. The residual was purified with silica gel column chromatography (chloroform/ethyl acetate) to obtain the substance of interest (1.00 g, yield: 89%, HPLC purity: 97.59 area %, HPLC area % of 2-acetylnaphtho[2,3-b]furan-4,9-dione: 1.06 area %).

$^1$H-NMR (400 MHz, CDCl$_3$) δ: 1.81 (s, 3H), 4.01-4.11 (m, 4H), 6.88 (s, 1H), 7.70-7.76 (m, 2H), 8.14-8.21 (m, 2H).

Step 1-2: Production of 2-acetylnaphtho[2,3-b]furan-4,9-dione

7% hydrochloric acid (0.2 mL) was added to an acetone (2.0 mL) suspension of 2-(2-methyl-1,3-dioxolane-2-yl)naphtho[2,3-b]furan-4,9-dione (100 mg) obtained in step 1-1. The suspension was heated and refluxed for 7 hours. After cooling the reaction suspension, 7% hydrochloric acid (2.0 mL) was added. The deposited solid was filtered. The deposited solid was washed with water and then subjected to vacuum drying to obtain the substance of interest (79 mg, yield: 94%, HPLC purity: 99.57 area %).

Aggregate yield based on 2-bromo-3-hydroxynaphthalene-1,4-dione: 84%

$^1$H-NMR (400 MHz, CDCl$_3$) δ: 2.64 (s, 3H), 7.59 (s, 1H), 7.77-7.81 (m, 2H), 8.20-8.26 (m, 2H).

Example 2: Production Method of 2-acetylnaphtho[2,3-b]furan-4,9-dione

[Chemical formula 30]

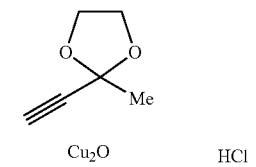

2-bromo-3-hydroxynaphthalene-1,4-dione (30.0 g) and copper(I) oxide (17.0 g; Aldrich) were placed in a flask. The gas was replaced with nitrogen. Pyridine (614 mL) was added. After raising the temperature to 100° C., 2-ethynyl-2-methyl-1,3-dioxolane (14.6 g) was dripped in over 1 hour. The reaction solution was heated and refluxed for 2 hours. After cooling the solution to 40° C., the suspension was filtered with Celite. The residual on the filter was washed with NMP (174 mL). The resulting two filtrates were combined and subjected to vacuum concentration. Pyridine (547 mL) was distilled, and NMP (261 mL) was added to the residual. After raising the temperature to 90° C., 35% hydrochloric acid (105 mL) was dripped in over 1 hour. The reaction solution was heated for 3 hours at 90° C. and cooled to 20° C. Water (370 mL) was added, and the suspension was filtered. The resulting wet crystal was washed with 50% ethanol water (136 mL) and ethanol (152 mL) in this order, and then subjected to vacuum drying to obtained the substance of interest (23.0 g, yield: 81%, HPLC purity: 99.48 area %).

Example 3: Production method of 2-(2-methyl-1,3-dioxane-2-yl)naphtho[2,3-b]furan-4,9-dione and 2-acetylnaphtho[2,3-b]furan-4,9-dione

[Chemical formula 31]

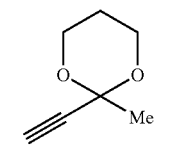

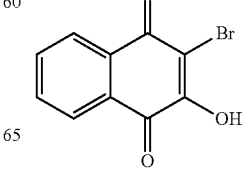

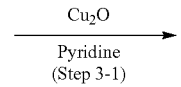

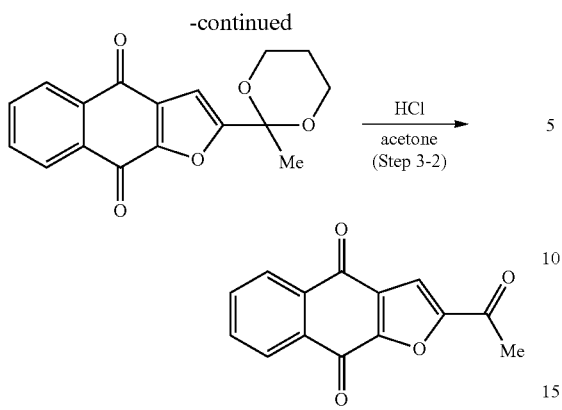

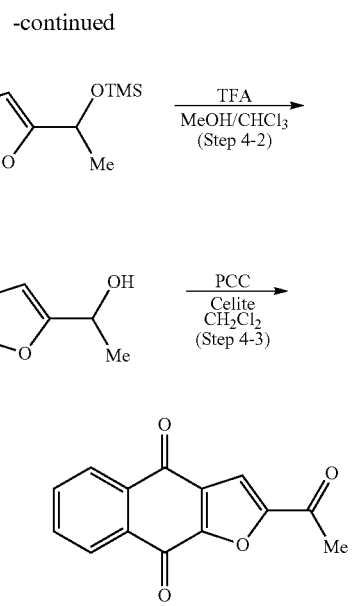

Step 3-1: Production of 2-(2-methyl-1,3-dioxane-2-yl)naphtho[2,3-b]furan-4,9-dione 2-bromo-3-hydroxynaphthalene-1,4-dione (109.2 mg) and copper(I) oxide (113.4 mg; Aldrich) were placed in a flask. The gas was replaced with nitrogen. Pyridine (4.94 mL) and 2-ethynyl-2-methyl-1,3-dioxane (75.3 mg) were added. The reaction solution was stirred for 1 hour at 25° C., and then heated and refluxed for 6 hours. After cooling the reaction solution at room temperature, 3.5% hydrochloric acid (20 mL) and ethyl acetate (20 mL) were added, and the organic layer was separated. The organic layer was washed with 3.5% hydrochloric acid (20 mL), dried with magnesium sulfate, and then subjected to vacuum concentration. The residual was purified with silica gel column chromatography (hexane/chloroform) to obtain the substance of interest (138.9 mg (including 21 wt % of diacetylene form), yield: 85%, HPLC purity: 98.60 area %, HPLC area % of 2-acetylnaphtho[2,3-b]furan-4,9-dione: 0.33 area %).

$^1$H-NMR (400 MHz, CDCl$_3$) δ: 1.35-1.40 (m, 1H), 1.64 (s, 3H), 2.05-2.18 (m, 1H), 3.86-3.89 (m, 2H), 3.90-4.02 (m, 2H), 6.95 (s, 1H), 7.71-7.77 (m, 2H), 8.15-8.24 (m, 2H).

Step 3-2: Production of 2-acetylnaphtho[2,3-b]furan-4,9-dione 2-(2-methyl-1,3-dioxane-2-yl)naphtho[2,3-b]furan-4,9-dione obtained in step 3-1 was used to obtain 2-acetylnaphtho[2,3-b]furan-4,9-dione (95.3 mg, yield: 100%, HPLC purity: 98.58 area %) in the same manner as step 1-2.

Aggregate yield based on 2-bromo-3-hydroxynaphthalene-1,4-dione: 85%

Example 4: Production method of 2-(1-((trimethylsilyl)oxy)ethyl)naphtho[2,3-b]furan-4,9-dione and 2-acetylnaphtho[2,3-b]furan-4,9-dione

[Chemical formula 32]

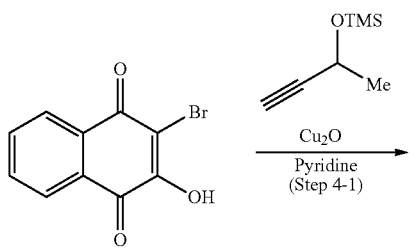

Step 4-1: Production of 2-(1-((trimethylsilyl)oxy)ethyl)naphtho[2,3-b]furan-4,9-dione 2-bromo-3-hydroxynaphthalene-1,4-dione (100.0 mg) and copper(I) oxide (111.5 mg; Aldrich) were placed in a flask. The gas was replaced with nitrogen. Pyridine (4.94 mL) and (but-3-yn-2-yloxy)trimethylsilane (70.1 mg; Alfa Aesar) were added. The solution was stirred for 1 hour at 25° C., and then heated and refluxed for 8 hours. After cooling the reaction solution to room temperature, 3.5% hydrochloric acid (20 mL) and ethyl acetate (20 mL) were added, and the organic layer was separated. The separated organic layer was washed with 3.5% hydrochloric acid (20 mL), dried with magnesium sulfate, and then subjected to vacuum concentration to obtain a solid 2-(1-((trimethylsilyl)oxy)ethyl)naphtho[2,3-b]furan-4,9-dione (140.6 mg).

Step 4-2: Production of 2-(1-hydroxyethyl)naphtho[2,3-b]furan-4,9-dione

The 2-(1-((trimethylsilyl)oxy)ethyl)naphtho[2,3-b]furan-4,9-dione obtained in step 4-1 was dissolved in chloroform (3 mL) and methanol (1 mL), and trifluoroacetic acid (60 μL) was added. The solution was stirred for 30 minutes to remove silyl groups. After the reaction solution was subjected to vacuum concentration, the residual was purified with silica gel column chromatography (chloroform/ethyl acetate) to obtain 2-(1-hydroxyethyl)naphtho[2,3-b]furan-4,9-dione (82.0 mg, yield from 2-bromo-3-hydroxynaphthalene-1,4-dione: 86%, HPLC purity: 98.78 area %).

$^1$H-NMR (400 MHz, CDCl$_3$) δ: 1.64 (d, 3H, J=6.4 Hz), 2.24 (d, 1H, J=5.2 Hz), 5.30 (qd, 1H, J=6.4 and 5.2 Hz), 6.84 (s, 1H), 7.71-7.76 (m, 2H), 8.14-8.21 (m, 2H).

Step 4-3: Production of 2-acetylnaphtho[2,3-b]furan-4,9-dione

Pyridinium chlorochromate (PCC, 109 mg) was added to a dichloromethane (2.1 mL) suspension of Celite (240 mg) and the 2-(1-hydroxyethyl)naphtho[2,3-b]furan-4,9-dione (24 mg) obtained in step 4-2 at −7.5° C., and the solution was stirred for 15 hours at the same temperature. The reaction solution was filtered to remove insoluble matters, and then washed with dichloromethane. The organic layer was subjected to vacuum concentration and the residual was purified by silica gel column chromatography (hexane/ethyl acetate) to obtain 2-acetylnaphtho[2,3-b]furan-4,9-dione (11 mg, yield: 47%, HPLC purity: 99.99 area %). Aggregate yield based on 2-bromo-3-hydroxynaphthalene-1,4-dione: 40%

Example 5: Production method of 2-(2-methyl-1,3-dixolane-2-yl)naphtho[2,3-b]furan-4,9-dione

[Chemical formula 33]

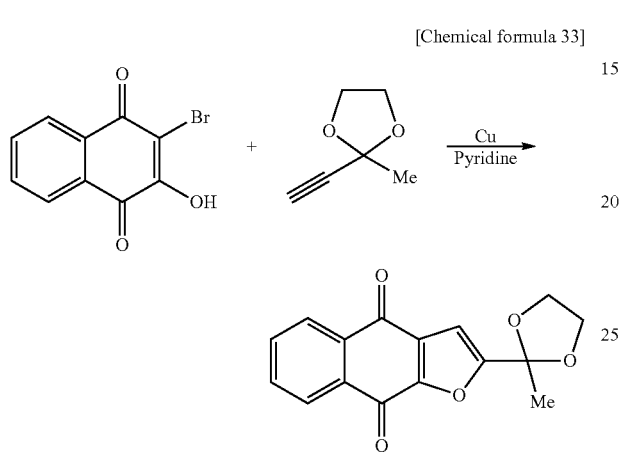

2-bromo-3-hydroxynaphthalene-1,4-dione (101 mg) and copper powder (51 mg; Kanto Chemical, 49525-52, 25 nm) were placed in a flask. The gas was replaced with nitrogen. Pyridine (4.9 mL) and 2-ethynyl-2-methyl-1,3-dioxolane (55 mg) were added. The reaction solution was stirred for 1 hour at 25° C., and then heated and refluxed for 6 hours. 23% hydrochloric acid (10 mL) was added to the reaction solution under ice cooling temperature, and the deposit was filtered out. The deposit was washed with 7% hydrochloric acid and subjected to vacuum drying to obtain 2-(2-methyl-1,3-dioxolane-2-yl)naphtho[2,3-b]furan-4,9-dione (100 mg, yield: 88%, HPLC purity: 97.64 area %, HPLC area % of 2-acetylnaphtho[2,3-b]furan-4,9-dione: 1.02 area %).

Example 6: Production method of 2-(1-((tert-butyldimethylsilyl)oxy)ethyl)naphtho[2,3-b]furan-4,9-dione and 2-(1-hydroxyethyl)naphtho[2,3-b]furan-4,9-dione

[Chemical formula 34]

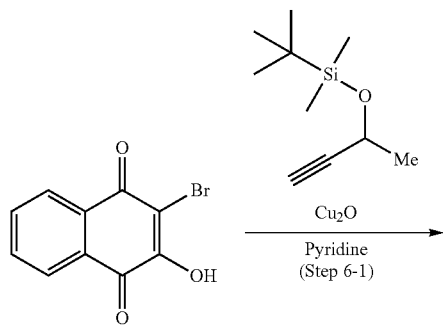

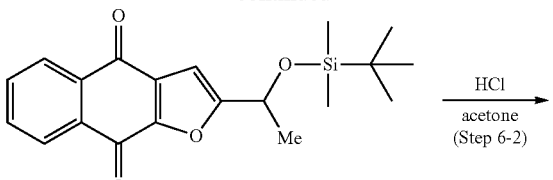

Step 6-1: Production of 2-(1-((tert-butyldimethylsilyl)oxy)ethyl)naphtho[2,3-b]furan-4,9-dione 2-bromo-3-hydroxynaphthalene-1,4-dione (100.7 mg) and copper(I) oxide (121.4 mg; Aldrich) were placed in a flask. The gas was replaced with nitrogen. Pyridine (4.94 mL) and (but-3-yn-2-yloxy)(tert-butyl)dimethylsilane (87.0 mg; Aldrich) were added. The reaction solution was stirred for 1 hour at 25° C., and then heated and refluxed for 6 hours. After cooling the reaction solution to room temperature, 3.5% hydrochloric acid (20 mL) and ethyl acetate (20 mL) were added, and the organic layer was separated. The organic layer was washed with 3.5% hydrochloric acid (20 mL), dried with magnesium sulfate, and then subjected to vacuum concentration to obtain 2-(1-((tert-butyldimethylsilyl)oxy)ethyl)naphtho[2,3-b]furan-4,9-dione (147.1 mg (9 wt. % of diacetylene mixed in), yield: 94%, HPLC purity: 96.74 area %, HPLC area % of 2-(1-hydroxyethyl)naphtho[2,3-b]furan-4,9-dione: 3.26 area %).

$^1$H-NMR (400 MHz, CDCl$_3$) δ: −0.04 (s, 3H), 0.00 (s, 3H), 0.80 (s, 9H), 1.43 (d, 3H, J=6.8 Hz), 4.01-4.11 (q, 1H, J=6.8 Hz), 6.66 (s, 1H), 7.58-7.62 (m, 2H), 8.04-8.09 (m, 2H).

Step 6-2: Production of 2-(1-hydroxyethyl)naphtho[2,3-b]furan-4,9-dione

7% hydrochloric acid (0.4 mL) was added to an acetone (2 mL) suspension of the 2-(1-((tert-butyldimethylsilyl)oxy)ethyl)naphtho[2,3-b]furan-4,9-dione (148.1 mg) obtained in step 6-1 and stirred for 2.5 hours at 60° C. The reaction solution was cooled and then 3.5% hydrochloric acid (10 mL) was added. The deposited crystal was filtered and washed with 3.5% hydrochloric acid, and vacuum dried. The crystal was purified with silica gel column chromatography (chloroform/ethyl acetate) to obtain 2-(1-hydroxyethyl)naphtho[2,3-b]furan-4,9-dione (65.0 mg, yield: 71%, HPLC purity: 99.88 area %).

Yield from 2-bromo-3-hydroxynaphthalene-1,4-dion: 67%

Example 7: Production method of 2-(1-((tetrahydro-2H-pyran-2-yl))oxy)ethyl)naphtho[2,3-b]furan-4,9-dione and 2-(1-hydroxyethyl)naphtho[2,3-b]furan-4,9-dione

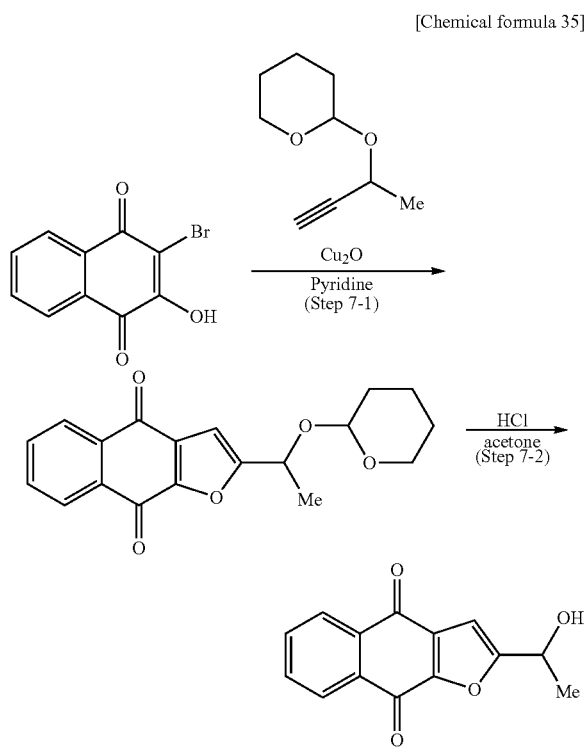

Step 7-1: Production of 2-(1-((tetrahydro-2H-pyran-2-yl))oxy)ethyl)naphtho[2,3-b]furan-4,9-dione 2-bromo-3-hydroxynaphthalene-1,4-dione (100.1 mg) and copper(I) oxide (121.4 mg; Aldrich) were placed in a flask. The gas was replaced with nitrogen. Pyridine (4.94 mL) and 2-(but-3-yn-2-yloxy)tetrahydro-2H-pyran (77.1 mg; Aldrich) were added. The solution was stirred for 1 hour at 25° C., and then heated and refluxed for 6 hours. After cooling the reaction solution to room temperature, 3.5% hydrochloric acid (20 mL) and ethyl acetate (20 mL) were added, and the organic layer was separated. The organic layer was washed with 3.5% hydrochloric acid (20 mL), dried with magnesium sulfate, and then subjected to vacuum concentration. The residual was purified with silica gel column chromatography (hexane/ethyl acetate) to obtain 2-(1-((tetrahydro-2H-pyran-2-yl))oxy)ethyl)naphtho[2,3-b]furan-4,9-dione (120.3 mg, yield: 93%, HPLC purity: 81.04 area %, HPLC area % of 2-(1-hydroxyethyl)naphtho[2,3-b]furan-4,9-dione: 18.38 area %).

$^1$H-NMR (400 MHz, CDCl$_3$) δ: 1.46-1.59 (m, 4H), 1.61 (d, 3H, J=6.8 Hz), 1.64-1.75 (m, 1H), 1.76-1.89 (m, 1H), 3.50-3.55 (m, 1H), 3.87-3.93 (m, 1), 4.66 (t, 1H, J=3.6 Hz), 5.17 (q, 1H, J=6.8 Hz), 6.80 (s, 1H), 7.68-7.75 (m, 2H), 8.12-8.22 (m, 2H).

Step 7-2: Production of 2-(1-hydroxyethyl)naphtho[2,3-b]furan-4,9-dione

The 2-(1-((tetrahydro-2H-pyran-2-yl))oxy)ethyl)naphtho[2,3-b]furan-4,9-dione (94.68 mg) obtained in step 7-1 was dissolved in acetone (2.0 mL), and 7% hydrochloric acid (0.4 mL) was added. After stirring for 3 hours at 60° C., methanol (1.0 mL) was added, and the solution was stirred for 1.5 hours. After cooling the reaction solution, 3.5% hydrochloric acid (10 mL) was added. The deposited crystal was filtered out and washed with 3.5% hydrochloric acid and dried. The crystal was purified with silica gel column chromatography (chloroform/ethyl acetate) to obtain 2-(1-hydroxyethyl)naphtho[2,3-b]furan-4,9-dione (51.8 mg, yield: 74%, HPLC purity: 99.99 area %).

Aggregate yield based on 2-bromo-3-hydroxynriaphtha-lene-1,4-dione: 69%

Comparative Example 1: Production of 2-(1-hydroxyethyl)naphtho[2,3-b]furan-4,9-dione and 2-acetylnaphtho[2,3-b]furan-4,9-dione 2-acetyalnaphtho[2,3-b]furan-4,9-dione was produced according to the method described in Non Patent Literature 1 as a Comparative Example. Specifically, the following method was used.

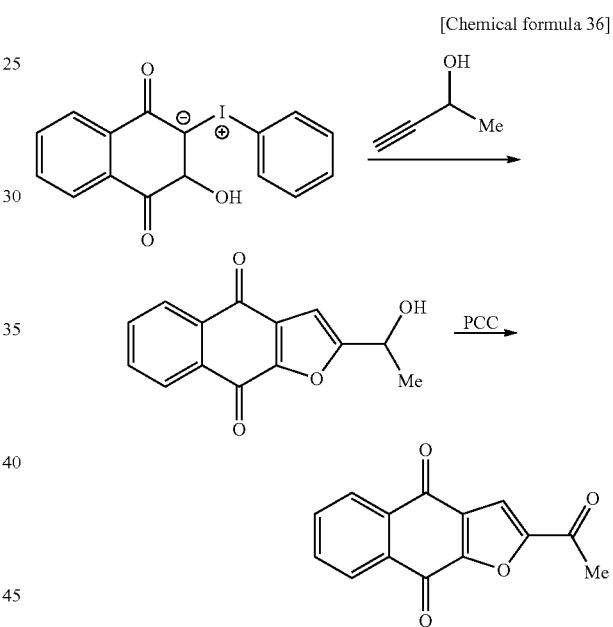

3-phenyliodonio-1,2,4-trioxo-1,2,3,4-tetrahydronaphtha-lenide (100.1 mg) was added to a pyridine (2.5 mL) solution of 3-butyne-2-ol (190.0 mg), palladium acetate (6.74 mg), copper(I) oxide (80.61 mg), and copper(I) bromide (37.76 mg) at 80° C. The reaction solution was stirred for 4 hours and then cooled to room temperature, and ethyl acetate was added. The organic layer was washed with 10% hydrochloric acid, aqueous saturated sodium carbonate solution, an aqueous sodium sulfite solution, and saturated saline. The organic layer was dried with anhydrous sodium sulphate and subjected to vacuum concentration. The residual was purified with silica gel column chromatography (chloroform) to obtain 2-(1-hydroxyethyl)naphtho[2,3-b]furan-4,9-dione (34.6 mg, yield: 54%, HPLC purity: 80.46 area %).

2-(1-hydroxyethyl)naphtho[2,3-b]furan-4,9-dione (24 mg) was dissolved in methylene chloride (2.1 mL) and cooled to −10° C. Pyridinium chlorochromate (109 mg) and Celite (240 mg) were added to the solution. The orange suspension was stirred for 17 hours, filtered, and subjected to vacuum concentration. The residual was purified with silica gel column chromatography (hexane/ethyl acetate) to obtain 2-acetylnaphtho[2,3-b]furan-4,9-dione (11 mg, yield: 47%, HPLC purity: 99.99 area %).

Aggregate yield based on 3-phenyliodonio-1,2,4-trioxo-1,2,3,4-tetrahydronaphthalenide: 25%

Comparative Example 2: Production of 2-acetyl-2,3-dihydronaphtho[2,3-b]furan-4,9-dione and 2-acetylnaphtho[2,3-b]furan-4,9-dione 2-acetylnaphtho[2,3-b]furan-4,9-dione was produced according to the method described in Patent Literature 2 as a Comparative Example. Specifically, the following method was used.

[Chemical formula 37]

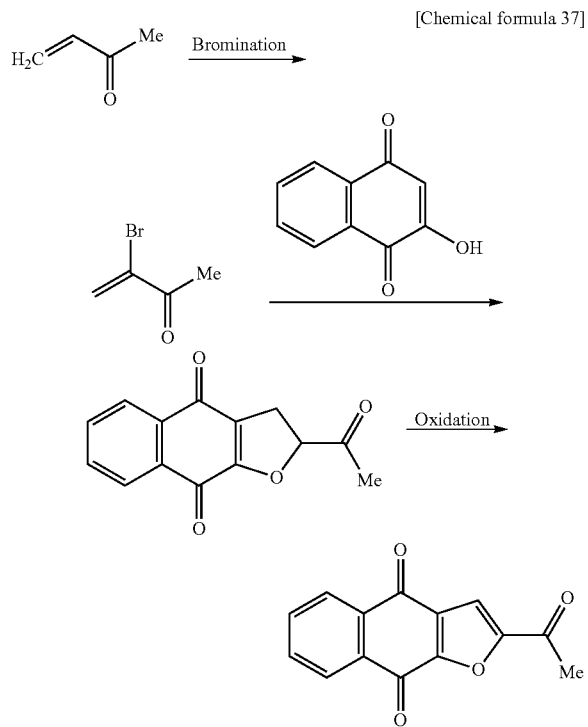

Methyl vinyl ketone (16.1 g) was added to a 300 mL flask containing dichloromethane (40 mL) cooled to −2° C. Bromine (36.7 g) was then dripped in over 25 minutes at 2 to 3° C. After washing the reaction solution with water (50 mL), the organic layer was dried with anhydrous sodium sulfate (5 g). After removing the anhydrous sodium sulfate, the organic layer was subjected to vacuum concentration. The resulting residual (48.8 g) was transferred into a 1 L flask using DMF (40 mL) and cooled to −2° C. DBU (27.3 g) was dripped into the DMF solution over 15 minutes, and DMF (50 mL) and 2-hydroxy-1,4-naphthoquinone (31.4 g) was added. The temperature was raised to room temperature under ambient atmosphere. DBU (25.8 g) was dripped into the reaction solution over 45 minutes at room temperature, and then DMF (50 mL) was added. The reaction solution was stirred for about 3 hours at room temperature and then cooled to 0° C. Water (500 mL) was added thereto. The deposited compound was filtered and washed with water (80 mL), aqueous 5% sodium carbonate solution (80 mL), water (80 mL), aqueous 2% acetic acid solution (80 mL) and ethanol (80 mL) in this order to obtain 2-acetyl-2,3-dihydronaphtho[2,3-b]furan-4,9-dione (21.1 g) (yield: 48%).

2-acetyl-2,3-dihydronaphtho[2,3-b]furan-4,9-dione (10.0 g), ethanol (250 mL), and DBU (5.1 g) were added to a 500 mL flask. The mixture was heated and refluxed for 30 minutes under ambient atmosphere. After the reaction solution was cooled to 0° C., water (250 mL) was added. The deposited crystal was obtained by filtering. The crystal was washed with water (10 mL), an aqueous 2% acetic acid solution (10 mL), and ethanol (10 mL) in this order, and subjected to vacuum drying to obtain a crystal of 2-acetylnaphtho[2,3-b]furan-4,9-dione (3.2 g, HPLC purity: 99.70 area %) (yield 32%).

Aggregate yield based on 2-hydroxy-1,4-naphthoquinone: 15%

As disclosed above, the present invention is exemplified by the use of the preferred embodiments of the present invention. However, it is understood that the scope of the present invention should be interpreted based solely on the Claims. The present application claims priority to Japanese Patent Application No. 2016-61242 (filed on Mar. 25, 2016). The entire content thereof is incorporated herein by reference. It is also understood that any patent, any patent application, and any references cited herein should be incorporated herein by reference in the same manner as the contents are specifically described herein.

INDUSTRIAL APPLICABILITY 2-alkylcarbonylnaphtho[2,3-b]furan-4,9-dione related substances that are useful as pharmaceutical products can be produced at a high yield, with a high purity, safely, and at low cost by using the production methods of the present invention.

The invention claimed is:
1. A compound of formula (I):

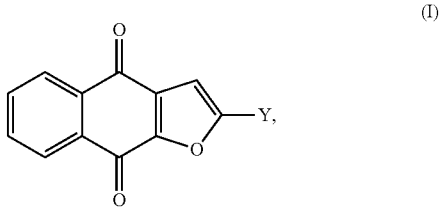

(I)

or a tautomer thereof, or an optionally pharmaceutically acceptable salt thereof, wherein Y is a group represented by the following formula (Ya), (Yb), or (Yc):

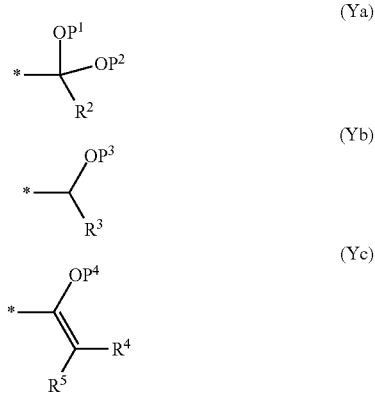

wherein
* denotes a bonding position;
$P^1$ and $P^2$ are identical or different, and each independently is selected from the group consisting of:
(1) a hydrogen atom, (2) an optionally substituted $C_{1-10}$alkyl group,
(3) a silyl group, wherein the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group,
(4) an optionally substituted $C_{6-10}$aryl group,
(5) an optionally substituted $C_{1-10}$alkylcarbonyl group,
(6) an optionally substituted $C_{6-10}$arylcarbonyl group, and
(7) an optionally substituted $C_{3-10}$cycloalkyl group; and wherein
when $P^1$ and $P^2$ are identical or different, and each independently an optionally substituted $C_{1-10}$alkyl group, an optionally substituted $C_{6-10}$aryl group, an optionally substituted $C_{1-10}$alkylcarbonyl group, or an optionally substituted $C_{3-10}$cycloalkyl group, or they may be taken together to form an optionally substituted cyclic ketal, wherein $P^1$ and $P^2$ are not both hydrogen atoms;

$P^3$ is selected from the group consisting of:
(1) a substituted $C_{1-10}$alkyl group,
(2) a silyl group, wherein the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group,
(3) an optionally substituted 3- to 12-membered monocyclic or polycyclic heterocyclic group, wherein in the heterocyclic group, a carbon atom adjacent to a heteroatom in the ring is bound to the oxygen atom to which $P^3$ in the formula (Yb) is attached,
(4) an optionally substituted $C_{2-10}$alkenyl group,
(5) an optionally substituted $C_{6-10}$aryl group,
(6) an optionally substituted $C_{1-10}$alkylcarbonyl group,
(7) an optionally substituted $C_{6-10}$arylcarbonyl group,
(8) an optionally substituted $C_{1-10}$alkyloxycarbonyl group,
(9) an optionally substituted $C_{6-10}$aryloxycarbonyl group,
(10) an optionally substituted $C_{2-10}$alkenyloxycarbonyl group,
(11) an optionally substituted aminocarbonyl group,
(12) an optionally substituted $C_{1-10}$alkylsulfonyl group,
(13) an optionally substituted $C_{6-10}$arylsulfonyl group, and
(14) a formyl group;

$P^4$ is selected from the group consisting of:
(1) an optionally substituted $C_{1-10}$alkyl group,
(2) a silyl group, wherein the silyl group is substituted with three substituents independently selected from the group consisting of an optionally substituted $C_{1-10}$alkyl group, an optionally substituted $C_{1-10}$alkoxy group, and an optionally substituted $C_{6-10}$aryl group,
(3) an optionally substituted 3- to 12-membered monocyclic or polycyclic heterocyclic group, wherein in the heterocyclic group, a carbon atom adjacent to a heteroatom in the ring is bound to the oxygen atom to which $P^4$ in the formula (Yc) is attached,
(4) an optionally substituted $C_{2-10}$alkenyl group,
(5) an optionally substituted $C_{6-10}$aryl group,
(6) an optionally substituted $C_{1-10}$alkylcarbonyl group,
(7) an optionally substituted $C_{6-10}$arylcarbonyl group,
(8) an optionally substituted $C_{1-10}$alkyloxycarbonyl group,
(9) an optionally substituted $C_{6-10}$aryloxycarbonyl group,
(10) an optionally substituted $C_{2-10}$alkenyloxycarbonyl group,
(11) an optionally substituted aminocarbonyl group,
(12) an optionally substituted $C_{1-10}$alkylsulfonyl group,
(13) an optionally substituted $C_{6-10}$arylsulfonyl group, and
(14) a formyl group;

$R^2$ is an optionally substituted $C_{1-10}$alkyl group;
$R^3$ is an optionally substituted $C_{1-10}$alkyl group; and
$R^4$ and $R^5$ are identical or different, and each independently a hydrogen atom, or an optionally substituted $C_{1-10}$alkyl group, with the proviso that 2-(2-methyl-1,3-dioxolane-2-yl)naphtho[2,3-b]furan-4,9-dione and 1-(4,9-dioxo-4,9-dihydronaphtho[2,3-b]furan-2-yl)ethyl acetate are excluded.

2. The compound according to claim 1, or a tautomer thereof, or an optionally pharmaceutically acceptable salt thereof,
wherein $P^1$ and $P^2$ are identical or different, and each independently selected from the group consisting of:
(1) a hydrogen atom,
(2) a $C_{1-6}$alkyl group optionally substituted with one to three groups independently selected from the group consisting of a halogen atom and a $C_{1-6}$alkoxy group,
(3) a silyl group optionally substituted with one to three $C_{1-6}$alkyl groups,
(4) a phenyl group,
(5) a benzyl group, and
(6) a $C_{1-6}$alkylcarbonyl group; or
$P^1$ and $P^2$ are taken together to form a cyclic ketal selected from the group consisting of:
(7) 1,3-dioxolane optionally substituted with one to four groups independently selected from the group consisting of a $C_{1-6}$alkyl group, a $C_{1-6}$alkoxy group, a hydroxyl group, and a phenyl group,
(8) 1,3-dioxolan-4-one,
(9) 1,3-dioxolane-4,5-dione,
(10) 1,3-dioxane optionally substituted with one to four groups independently selected from the group consisting of a $C_{1-6}$alkyl group, a $C_{1-6}$alkoxy group, a hydroxyl group, and a phenyl group,
(11) 1,3-dioxane-4-one,
(12) 1,3-dioxane-4,6-dione, and
(13) benzo[d][1,3]dioxole.

3. The compound according to claim 2, or a tautomer thereof, or an optionally pharmaceutically acceptable salt thereof, wherein $P^1$ and $P^2$ are identical or different, and each independently a $C_{1-6}$alkyl group or a $C_{1-6}$alkylcarbonyl group, or $P^1$ and $P^2$ are taken together to form a cyclic ketal selected from the group consisting of 1,3-dioxolane optionally substituted with one to four $C_{1-6}$alkyl groups, and 1,3-dioxane optionally substituted with one to four $C_{1-6}$alkyl groups.

4. The compound according to claim 3, or a tautomer thereof, or an optionally pharmaceutically acceptable salt thereof, wherein $P^1$ and $P^2$ are taken together to form 1,3-dioxane.

5. The compound according to claim 1, or a tautomer thereof, or an optionally pharmaceutically acceptable salt thereof, wherein $R^2$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

6. The compound according to claim 5, or a tautomer thereof, or an optionally pharmaceutically acceptable salt thereof, wherein $R^2$ is a methyl group.

7. The compound according to claim 1, or a tautomer thereof, or an optionally pharmaceutically acceptable salt thereof, wherein $P^3$ is selected from the group consisting of:

(1) a $C_{1-6}$alkyl group, wherein the alkyl group is substituted with one to three groups independently selected from the group consisting of:
  (a) a halogen atom,
  (b) a $C_{1-6}$alkoxy group,
  (c) a silyloxy group substituted with three substituents independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group;
(2) a silyl group substituted with three substituents independently selected from the group consisting of a $C_{1-6}$alkyl group and a phenyl group;
(3) a 3- to 8-membered monocyclic heterocyclic group, wherein the heterocyclic group has at least one or more oxygen atoms in the ring and a carbon atom adjacent to the oxygen atom(s) is bound to the oxygen atom to which $P^3$ in the formula (Yb) is attached;
(4) a $C_{2-6}$alkenyl group;
(5) a phenyl group, wherein the phenyl group is optionally substituted with one to three groups independently selected from the group consisting of a halogen atom, a nitro group, and a $C_{1-6}$alkoxy group;
(6) a $C_{1-6}$alkylcarbonyl group, wherein the alkyl is optionally substituted with one to three groups independently selected from the group consisting of a halogen atom, a hydroxyl group, a phenoxy group, a phenyl group, and a $C_{1-6}$alkoxy group;
(7) a phenylcarbonyl group, wherein the phenyl is optionally substituted with one to three groups independently selected from the group consisting of a halogen atom, a hydroxyl group, a nitro group, a $C_{1-6}$alkyl group, and a $C_{1-6}$alkoxy group;
(8) a $C_{1-6}$alkyloxycarbonyl group, wherein the alkyl is optionally substituted with one to three groups independently selected from the group consisting of a halogen atom, a hydroxyl group, a $C_{1-6}$alkoxy group, and a phenyl group;
(9) a phenyloxycarbonyl group, wherein the phenyl is optionally substituted with one to three groups independently selected from the group consisting of a halogen atom, a hydroxyl group, a nitro group, a $C_{1-6}$alkyl group, and a $C_{1-6}$alkoxy group;
(10) a $C_{2-6}$alkenyloxycarbonyl group;
(11) an aminocarbonyl group, wherein the amino is optionally substituted with one to two groups independently selected from the group consisting of a C1-6alkyl group and a phenyl group;
(12) a $C_{1-6}$alkylsulfonyl group;
(13) a phenylsulfonyl group, wherein the phenyl is optionally substituted with one to three $C_{1-6}$alkyl groups; and
(14) a formyl group.

8. The compound according to claim 7, or a tautomer thereof, or an optionally pharmaceutically acceptable salt thereof,
wherein $P^3$ is selected from the group consisting of
(1) a $C_{1-6}$alkyl group substituted with one to three $C_{1-6}$alkoxy groups;
(2) a silyl group substituted with three substituents independently selected from the group consisting of a $C_{1-6}$alkyl group and a phenyl group; and
(3) a 5- or 6-membered monocyclic saturated heterocyclic group, wherein the heterocyclic group has at least one or more oxygen atoms in the ring and a carbon atom adjacent to the oxygen atom(s) is bound to the oxygen atom to which $P^3$ in the formula (Yb) is attached.

9. The compound according to claim 8, or a tautomer thereof, or an optionally pharmaceutically acceptable salt thereof, wherein $P^3$ is a 2-tetrahydropyranyl group, a trimethylsilyl group, or a tert-butyldimethylsilyl group.

10. The compound according to claim 1, or a tautomer thereof, or an optionally pharmaceutically acceptable salt thereof, wherein $R^3$ is a $C_{1-10}$alkyl group optionally substituted with one to three groups independently selected from the group consisting of a halogen atom, a hydroxyl group, a $C_{1-6}$alkoxy group, a $C_{3-10}$cycloalkyl group, a $C_{6-10}$aryl group, and a 3- to 12-membered monocyclic or polycyclic heterocyclic group.

11. The compound according to claim 10, or a tautomer thereof, or an optionally pharmaceutically acceptable salt thereof, wherein $R^3$ is a methyl group.

12. The compound according to claim 1, or a tautomer thereof, or an optionally pharmaceutically acceptable salt thereof, wherein $P^4$ is selected from the group consisting of:
(1) a $C_{1-6}$alkyl group, wherein the alkyl group is optionally substituted with one to three groups independently selected from the group consisting of:
  (a) a halogen atom,
  (b) a $C_{1-6}$alkoxy group,
  (c) a silyloxy group substituted with three groups independently selected from the group consisting of a $C_{1-6}$alkyl group and a phenyl group,
  (d) a silyl group substituted with three groups independently selected from the group consisting of a $C_{1-6}$alkyl group and a phenyl group, and
  (e) a phenyl group optionally substituted with one to three groups independently selected from the group consisting of a halogen atom, a methoxy group, and a nitro group;
(2) a silyl group substituted with three substituents independently selected from the group consisting of a $C_{1-6}$alkyl group and a phenyl group;
(3) a 3- to 8-membered monocyclic heterocyclic group, wherein the heterocyclic group has at least one or more oxygen atoms in the ring and a carbon atom adjacent to the oxygen atom(s) is bound to the oxygen atom to which $P^4$ in the formula (Yc) is attached;
(4) a $C_{2-6}$alkenyl group;
(5) a phenyl group, wherein the phenyl group is optionally substituted with one to three groups independently selected from the group consisting of a halogen atom, a nitro group, and a $C_{1-6}$alkoxy group;
(6) a $C_{1-6}$alkylcarbonyl group, wherein the alkyl is optionally substituted with one to three groups independently selected from the group consisting of a halogen atom, a hydroxyl group, a phenoxy group, a phenyl group, and a $C_{1-6}$alkoxy group;
(7) a phenylcarbonyl group, wherein the phenyl is optionally substituted with one to three groups independently selected from the group consisting of a halogen atom, a hydroxyl group, a nitro group, a $C_{l-6}$alkyl group, and a $C_{1-6}$alkoxy group;
(8) a $C_{1-6}$alkyloxycarbonyl group, wherein the alkyl is optionally substituted with one to three groups independently selected from the group consisting of a halogen atom, a hydroxyl group, a $C_{1-6}$alkoxy group, and a phenyl group;
(9) a phenyloxycarbonyl group, wherein the phenyl is optionally substituted with one to three groups independently selected from the group consisting of a halogen atom, a hydroxyl group, a nitro group, a $C_{1-6}$alkyl group, and a $C_{1-6}$alkoxy group;
(10) a $C_{2-6}$alkenyloxycarbonyl group;
(11) an aminocarbonyl group, wherein the amino is optionally substituted with one to two groups independently selected from the group consisting of a $C_{1-6}$alkyl group and a phenyl group;
(12) a $C_{1-6}$alkylsulfonyl group;

(13) a phenylsulfonyl group, wherein the phenyl is optionally substituted with one to three $C_{1-6}$alkyl groups; and
(14) a formyl group.

13. The compound according to claim 12, or a tautomer thereof, or an optionally pharmaceutically acceptable salt thereof,
wherein $P^4$ is selected from the group consisting of:
(1) a $C_{1-6}$alkyl group optionally substituted with one to three $C_{1-6}$alkoxy groups;
(2) a silyl group substituted with three substituents independently selected from the group consisting of a $C_{1-6}$alkyl group and a phenyl group; and
(3) a 5- or 6-membered monocyclic saturated heterocyclic group, wherein the heterocyclic group has at least one or more oxygen atoms in the ring and a carbon atom adjacent to the oxygen atom(s) is bound to the oxygen atom to which $P^4$ in the formula (Yc) is attached.

14. The compound according to claim 13, or a tautomer thereof, or an optionally pharmaceutically acceptable salt thereof, wherein $P^4$ is a 2-tetrahydropyranyl group, a trimethylsilyl group, or a tert-butyldimethylsilyl group.

15. The compound according to claim 14, or a tautomer thereof, or an optionally pharmaceutically acceptable salt thereof, wherein $R^4$ and $R^5$ are identical or different, and each independently selected from the group consisting of:
(1) a hydrogen atom, and
(2) a $C_{1-6}$alkyl group.

16. The compound according to claim 15, or a tautomer thereof, or an optionally pharmaceutically acceptable salt thereof, wherein $R^4$ and $R^5$ are hydrogen atoms.

17. The compound according to claim 1, or a tautomer thereof, or an optionally pharmaceutically acceptable salt thereof, wherein Y is a group represented by the formula (Ya) or (Yb).

18. The compound according to claim 1, or a tautomer thereof, or an optionally pharmaceutically acceptable salt thereof, wherein Y is a group represented by the formula (Ya) or (Yb), wherein
$P^1$ and $P^2$ are taken together to form a cyclic ketal selected from the group consisting of 1,3-dioxolane optionally substituted with one to four $C_{1-6}$alkyl groups, and 1,3-dioxane optionally substituted with one to four $C_{1-6}$alkyl groups;
$R^2$ is a $C_{1-6}$alkyl group;
$P^3$ is
(1) a silyl group substituted with three substituents independently selected from the group consisting of a $C_{1-6}$alkyl group and a phenyl group, or
(2) a 5- or 6-membered monocyclic saturated heterocyclic group, wherein the heterocyclic group has at least one or more oxygen atoms in the ring and a carbon atom adjacent to the oxygen atom(s) is bound to the oxygen atom to which $P^3$ in the formula (Yb) is attached; and
$R^3$ is a $C_{1-6}$alkyl group.

19. The compound according to claim 1, or a tautomer thereof, or an optionally pharmaceutically acceptable salt thereof, wherein Y is a group represented by the formula (Ya).

* * * * *